United States Patent [19]

Hu et al.

[11] Patent Number: 5,981,211
[45] Date of Patent: Nov. 9, 1999

[54] MAINTAINING CELLS FOR AN EXTENDED TIME BY ENTRAPMENT IN A CONTRACTED MATRIX

[75] Inventors: Wei-Shou Hu, Falcon Heights; Frank Bernard Cerra, Edina; Scott Lyle Nyberg, St. Louis Park; Matthew Thomas Scholz, Woodbury; Russell A. Shatford, Minneapolis, all of Minn.

[73] Assignee: Regents of the University of Minnesota, Minneapolis, Minn.

[21] Appl. No.: 08/726,652

[22] Filed: Oct. 7, 1996

Related U.S. Application Data

[62] Division of application No. 08/376,095, Jan. 20, 1995, Pat. No. 5,605,835, which is a continuation of application No. 07/864,893, Apr. 3, 1992, abandoned, which is a continuation-in-part of application No. 07/355,115, May 18, 1989, abandoned, which is a continuation-in-part of application No. 07/197,700, May 23, 1988, abandoned, and a continuation-in-part of application No. 07/605,371, Oct. 29, 1990, abandoned.

[51] Int. Cl.$^6$ .............................. C12P 1/00; C12M 3/00; C12N 5/00; C12N 11/04
[52] U.S. Cl. ......................... 435/41; 435/70.1; 435/177; 435/182; 435/325; 435/363; 435/382; 435/395; 435/396; 435/400; 435/401; 435/289.1; 435/297.2; 435/297.4; 435/813
[58] Field of Search ............................. 435/41, 174, 177, 435/178, 182, 382, 395, 396, 398, 400, 401, 289.1, 297.1, 297.2; 425/70.1, 325, 363, 297.4

[56] References Cited

U.S. PATENT DOCUMENTS

| | | | |
|---|---|---|---|
| 3,186,917 | 6/1965 | Gerhardt et al. | 1995/1 |
| 3,734,851 | 5/1973 | Matsumura | 210/22 |
| 3,821,087 | 6/1974 | Knazek et al. | 195/127 |
| 3,875,008 | 4/1975 | Yoshino et al. | 195/63 |
| 3,883,393 | 5/1975 | Knazek et al. | 195/1.8 |
| 3,898,158 | 8/1975 | Miller | 210/22 |
| 3,997,396 | 12/1976 | DeLente | 195/1.8 |
| 4,184,922 | 1/1980 | Knazek et al. | 435/284 |
| 4,200,689 | 4/1980 | Knazek et al. | 435/2 |
| 4,206,015 | 6/1980 | Knazek et al. | 435/2 |
| 4,220,725 | 9/1980 | Knazek et al. | 435/285 |
| 4,225,671 | 9/1980 | Puchinger et al. | 435/71 |
| 4,242,459 | 12/1980 | Chick et al. | 435/283 |
| 4,242,460 | 12/1980 | Chick et al. | 435/284 |
| 4,353,888 | 10/1982 | Sefton | 424/25 |
| 4,378,017 | 3/1983 | Kosugi et al. | 424/35 |
| 4,407,957 | 10/1983 | Lim | 435/178 |
| 4,411,866 | 10/1983 | Kanno | 422/25 |
| 4,495,288 | 1/1985 | Jarvis, Jr. et al. | 435/241 |
| 4,537,860 | 8/1985 | Tolbert et al. | 435/240 |
| 4,546,083 | 10/1985 | Meyers et al. | 435/240 |
| 4,559,304 | 12/1985 | Kasai et al. | 435/240 |
| 4,582,799 | 4/1986 | Jarvis, Jr. | 435/68 |
| 4,588,407 | 5/1986 | Isono et al. | 623/11 |
| 4,603,109 | 7/1986 | Lillo | 435/41 |
| 4,634,447 | 1/1987 | Isono et al. | 623/66 |
| 4,639,422 | 1/1987 | Geimer et al. | 435/286 |
| 4,640,895 | 2/1987 | Davis | 435/296 |
| 4,643,715 | 2/1987 | Isono et al. | 604/4 |
| 4,647,536 | 3/1987 | Mosbach et al. | 435/177 |
| 4,649,117 | 3/1987 | Familletti | 435/313 |
| 4,649,118 | 3/1987 | Anderson | 435/316 |
| 4,661,458 | 4/1987 | Berry et al. | 435/284 |
| 4,663,286 | 5/1987 | Tsang et al. | 435/178 |
| 4,675,002 | 6/1987 | Viles et al. | 604/5 |
| 4,692,411 | 9/1987 | Ghose | 435/243 |
| 4,703,108 | 10/1987 | Silver et al. | 530/356 |
| 4,743,545 | 5/1988 | Torobin | 435/41 |
| 4,764,471 | 8/1988 | Ripka | 435/255 |
| 4,861,485 | 8/1989 | Fecondini | 210/641 |

(List continued on next page.)

FOREIGN PATENT DOCUMENTS

| | | |
|---|---|---|
| 155237 | 9/1985 | European Pat. Off. . |
| 363262 | 4/1990 | European Pat. Off. . |
| 2565349 | 12/1985 | France . |
| 0018179 | 1/1985 | Japan . |
| 2071755 | 3/1990 | Japan . |
| 2178447 | 2/1987 | United Kingdom . |
| WO8900188 | 1/1989 | WIPO . |
| 8901967 | 3/1989 | WIPO . |
| 11529 | 11/1989 | WIPO . |

OTHER PUBLICATIONS

Charles Lee et al., "Exchange Transfusion in Hepatic Coma: Report of a Case", *Medical Journal of Australia*, (Jan. 11, 1958), pp. 40–42.

(List continued on next page.)

*Primary Examiner*—David M. Naff
*Attorney, Agent, or Firm*—Sughrue, Mion, Zinn, Macpeak & Seas, PLLC

[57] ABSTRACT

Methods of maintaining animal cells for product production, for supporting hepatocyte function and viability to treat a patient suffering from hepatic failure and for preserving tissue-specific function of mammalian cells are carried out with a bioreactor containing a feed and waste chamber and a cell chamber separated by a selectively permeable membrane. Within the cell chamber, a biocompatible contracted three-dimensional gel matrix entraps animal cells or genetic modifications thereof, and a liquid phase contains a concentrated solution of the cell product. The bioreactor uses only two chambers to achieve three distinct zones within the bioreactor. The bioreactor can be of either hollow fiber or flat-bed configuration. In the configuration using hollow fibers, the two fluid paths correspond to the cavity surrounding the hollow fibers (the extracapillary space), and to the lumens of the hollow fibers themselves. Both fluid paths have inlet and outlet ports. Communication between the two fluid paths is across the permeable medium—the hollow fiber material. To prepare a bioartificial liver, hepatocytes are inoculated into the hollow fibers in a solution which quickly forms a highly porous gel. The gel subsequently contracts, leaving an open channel within the hollow fiber adjacent to the gel core entrapped hepatocytes. This channel can be perfused with nutrient media for hepatocytes. The channel can also serve as a waste stream to remove toxins that the hepatocytes have modified to a water soluble form.

22 Claims, 21 Drawing Sheets

U.S. PATENT DOCUMENTS

| | | | |
|---|---|---|---|
| 4,923,598 | 5/1990 | Schal | 210/87 |
| 4,955,857 | 9/1990 | Shettigar | 604/5 |
| 4,975,375 | 12/1990 | Haruta et al. | 435/482 |
| 4,997,443 | 3/1991 | Walthall et al. | 623/11 |
| 5,043,260 | 8/1991 | Jauregui | 435/1 |
| 5,595,909 | 1/1997 | Hu et al. | 435/297.4 |

OTHER PUBLICATIONS

B. Eiseman et al., "Heterologous Liver Perfusion in Treatment of Hepatic Failure". *Annals of Surgery*, (Sep. 1965), pp. 329–345.

Sen et al., "Use of Isolated Perfused Cadaveric LIver in the Manangement of Hepatic Failure" *Surgery* (May 1966), vol. 59, No. 5, pp. 774–781.

Trey et al., "Treatment of Hepatic Coma By Exchange Blood Transfusion", *New England Journal of Medicine*, (Mar. 1966), vol. 274, pp. 473–481.

Burnell et al., "Acute Hepatic Coma Treated By Cross–Circulation or Exchange Transfusion", *New England Journal of Medicine*, (Apr. 1967), vol. 276, pp. 935–943.

Sabin et al., "Treatment of Hepatic Coma in Cirrhosis by Plasmapheresis and Plasma Infusion", *Annals of Internal Medicine*, (Jan. 1968), vol. 68, pp. 1–7.

Wolf et al., "Bilirubin Conjugation By An Artificial Liver Composed Of Cultured Cells And Synthetic Capillaries", *Trans.Amer.Soc.Artif. Int. Organs*, (1975), vol. XXI, pp. 16–27.

Opolon et al., "Hepatic Failure Coma (HFC) Treated By Polyacrylonitrile Membrane (PAN) Hemodialysis (HD)", *Irans.Amer.Soc.Artif.Int. Organs*, (1976), vol. XXII, pp. 701–710.

Aden et al., "Controlled Synthesis of HBsAg in a Differentiated Human Liver Carcinoma–Derived Cell Line", *Nature*, (Dec. 1979), vol. 282, pp. 615–616.

Knowles et al., "Human Hepatocellular Carcinoma Cell Lines Secrete the Major Plasma Proteins and Hepatitis B Surface Antigen", *Science*, (Jul. 1980), vol. 209, pp. 497–499.

Rojkind et al., "Connective Tissue Biomatrix: Its Isolation and Utilization for Long–Term Cultures of Normal Rat Hepatocytes", *Journal of Cell Biology*, (Oct. 1980), vol. 87, pp. 255–263.

Rueff et al., "Acute Hepatic Necrosis and Fulminant Hepatic Failure", *Gut*, (1973), vol. 14, pp. 805–815.

Reid et al., Culturing Hepatocytes and Other Differentiated Cells, *Hepatology*, (1984), vol. 4, No. 3, pp. 548–559.

Antonio Martinez–Hernandez, "The Hepatic Extracellular Matrix", *Laboratory Investigation*, (1984) vol. 51, No. 1, pp. 57–74.

Jefferson et al., "Posttranscriptional Modulation of Gene Expression in Cultured Rat Hepatocytes", *Molecular and Cellular Biology*, (Sep. 1984), vol. 4, No. 9, pp. 1929–1934.

Friedman et al., "Hepatic Lipocytes: The Principal Collagen–Producing Cells of Normal Rat Liver", *Proc. Natl. Acad. Sci. USA*, (Dec. 1985), vol. 82, pp. 8681–8685.

Lie et al., "Successful Treatment of Hepatic Coma By A New Artificial Liver Device In The Pig", *Res. Exp. Med.*, (1985), pp. 483–494.

O'Shea et al., "Encapsulation of Rat Islets of Langerhans Prolongs Xenograft Survival in Diabetic Mice", *Diabetes*, (Aug. 1986), vol. 35, pp. 943–946.

Ishihara et al., "Transport of Heparan Sulfate Into The Nuclei of Hepatocytes", *Journal of Biological Chemistry*, (1986), vol. 261, No. 29, pp. 13575–13580.

Geerts et al., "Immunogold Localization Of Procollagen III, Fibronectin and Heparan Sulfate Proteoglycan On Ultrathin Frozen Sections Of The Normal Rat Liver"., *Histochemistry*, (1986), pp. 355–362.

Sun et al., "Microencapsulated Hepatocytes As A Bioartificial Liver", *Trans.Am.Soc.Artif.Intern.Organs*, (1986), vol. XXXII, pp. 39–41.

Matsumura et al., "Hybrid Bioartificial Liver In Hepatic Failure: Preliminary Clinical Report" *Surgery*, (1987), pp. 99–103.

Spray et al., "Proteoglycans and Glycosaminoglycans Induce Gap Junction Synthesis and Function in Primary Liver Cultures", *The Journal of Cell Biology*, (Jul. 1987), vol. 105, pp. 541–551.

Busuttil et al., "The First 100 Liver Transplants At UCLA", *Annals of Surgery*, (1987), vol. 206, No. 4, pp. 387–402.

Sun et al., "Microencapsulated Hepatocytes: An In Vitro and In Vivo Study", *Biomat., Art. Cells, Art. Org.*, (1987), 15(2), pp. 483–496.

Dich et al., "Long–Term Culture of Hepatocytes: Effect Of Hormones On Enzyme Activities and Metabolic Capacity"., *Hepatology*, (1988), vol. 8, No. 1, pp. 39–45.

Blake et al., "Accuracy of Death Certificates In The Diagnosis of Alcoholic Liver Cirrhosis", *Alcoholism: Clinical and Experimental Research*, (Jan.–Feb. 1988), vol. 12, No. 1, pp. 168–172.

Muzzarelli et al., "Biological Activity of Chitosan: Ultrastructural Study", *Biomaterials*, (May 1988), vol. 9, pp. 247–252.

Cai et al., "Microencapsulated Hepatocytes For Bioartificial Liver Support", *Artificial Organs*, (May 1988), vol. 12, No. 5, pp. 388–393.

Shellman et al., "Prognosis Of Patients With Cirrhosis And Chronic Liver Disease Admitted To The Medical Intensive Care Unit", *Critical Care Medicine* (Jul. 1988), vol. 16, No. 7., pp. 671–678.

Arenson et al., "Formation Of Extracellular Matrix In Normal Rat Liver: Lipocytes As A Major Source of Proteoglycan", *Gastroenterology*, (1988), vol. 95, No. 2, pp. 441–447.

Saksela et al., "Endothelial Cell–Derived Heparan Sulfate Binds Basic Fibroblast Growth Factor And Protects It From Proteolytic Degradation", *Journal of Cell Biology* (Aug. 1988), vol. 107, pp. 743–751.

Warren et al., "Influence Of Medium Composition On 7–Alkoxycoumarin O–Dealkylase Activities Of Rat Hepatocytes In Primary Maintenance Culture", *Xenobiotica*, (1988), vol. 18, No. 8, pp. 973–981.

Goulet et al., "Cellular Interactions Promote Tissue–Specific Function, Biomatrix Deposition And Junctional Communication of Primary Cultured Hepatocytes", *Hepatology*, (1988), vol. 8, No. 5., pp. 1010–1018.

J.J. Maher, "Primary Hepatocyte Culture: Is It Home Away From Home?", *Hepatology*, (1988), vol. 8 No. 5, pp. 1162–1166.

Gordon et al., "Heparan Sulfate Is Necessary For Adhesive Interactions Between Human Early Hemopoietic Progenitor Cells . . . Microenvironment", *Leukemia* (1988), , vol. 2, No. 12, pp. 804–809.

Bissell et al., "The Role of Extracellular Matrix In Normal Liver", *Gastroenterol*, (1988), pp. 1–7.

Wong et al., "The Viability and Regeneration of Artificial Cell Microencapsulated Rat Hepatocyte Xenograft Transplants in Mice", *Biomat., Art.Cells., Art. Org.*, (1988), vol. 16, No. 4. pp. 731–739.

Tompkins et al., "Enzymatic Function of Alginate Immobilized Rat Hepatocytes", *Biotechnology and Bioengineering*, (1988), vol. 31, pp. 11–18.

Miura et al., "Liver Functions in Hepatocytes Entrapped Within Calcium Alginate", *Annals New York Academy of Sciences*, pp. 521–533.

Kashani et al., "Release of Hepatic Stimulatory Substance From Cultures Of Free And Microencapsulated Hepatocytes: Preliminary Report", *Biomat., Art Cells, Art. Org.*, (1988), vol. 16, No. 4, pp. 741–746.

Uchino et al., "A Hybrid Bioartificial Liver Composed of Multiplated Hepatocyte Monolayers", *ASAIO Transactions*, (1988), vol. 34, pp. 972–977.

Lanford et al., "Analysis of Plasma Protein and Lipoprotein Synthesis In Long–Term Primary Cultures of . . . Medium", *In Vitro Cellular & Developmental Biology*, (Feb. 1989), vol. 25, No. 2, pp. 174–182.

Dunn et al., "Hepatocyte Function And Extracellular Matrix Geometry: Long–Term Culture In A Sandwich Configuration", *FASEB J.* (1989), vol. 3, pp. 174–177.

Kelly et al., "Modulation of The Liver Specific Phenotype In The Human Hepatoblastoma Line HEP G2", *In Vitro Cellular & Developmental Biology*, (Feb. 1989), vol. 25, No. 2, pp. 217–222.

Saito et al., "Transplantation of Spheroidal Aggregate Cultured Hepatocytes Into The Rat Spleen", *Transplantation Proceedings*, (1989), vol. 21, No. 1, pp. 2374–2377.

Koide et al., "Continued High Albumin Production By Multicellular Spheroids Of Adult Rat Hepatocytes . . . Proteoglycans", *Biochemical and Biophysical Research Comm.*, (May 1989), vol. 161, No. 1., pp. 385–391.

Margulis et al., "Temporary Organ Substitution By Hemoperfusion Through Suspension . . . Insufficiency", *Resuscitation*, (1989), vol. 18, pp. 85–94.

Scholtz et al., "A Two–Compartment Cell Entrapment Bioreactor With Three Different Holding Times For Cells . . . Compounds", *Cyotechnology*, (1990), vol. 4, pp. 127–137.

Arnaout et al., "Development Of Bioartifical Liver: Bilirubin Conjugation In Gunn Rats", *Journal of Surgical Research*, (1990), vol. 48, pp. 379–382.

Hager et al., "A Prototype For A Hybrid Artificial Liver", *Trans.Am. Soc. Artif.Intern.Organs*, (1978), vol. XXIV, pp. 250–253.

Klement et al., "Construction Of A Large Scale Membrane Reactor System . . . Product", *Develop. Biol. Standard*, (1987), vol. 66, pp. 221–226.

Bell., et al., "Production of a Tissue–Like Structure by Contraction . . . Vitro", *Proc. Natl. Acad. Sci USA*, (Mar. 1979), vol. 76, No. 3, pp. 1274–1278.

Clouse et al., "The Regulation of Hemostasis: The Protein C System", *New England Journal Of Medicine*, (May 1986), vol. 314, No. 20, pp. 1298–1304.

Comp et al., "Plasma Proteins C and S: The Function and Assay of Two Natural Anticoagulants", *Laboratory Management*, (Dec. 1985), pp. 29–32.

Himes et al., "Attachment and Growth of Mammalian Cells on Microcarriers with Different Ion Exchange Capacities", *Biotechnology and Bioengineering*, (1987), vol. XXIX, pp. 1155–1163.

Jauregui et al., "Adult Rat Hepatocyte Cultures as The Cellular Component of an Artificial Hybrid Liver", in Paul, J.P. (Ed.), *Biomaterials in Artificial Organs*, (MacMillan), 1983, pp. 130–140.

Jauregui et al., "Hybrid Artificial Liver", in Szycher, M. (Ed.), *Biocompatible Polymers, Metals and Other Composites*, (1983), pp. 907–928.

Wang et al., "Fermentation and Enzyme Technology", John Wiley & Sons, (1979), p. 320.

Laskin, Allen, "Enzymes and Immobilized Cells in Biotechnology", The Benjamin Cumings Publishing Co., Inc., (1985), pp. 39–40.

Robertson et al. Dual Aerobic Hollow–Fiber Bioreactor for Cultivation of *Streptomyces Aureofaciens*, Biotechnology and Bioengineering, vol. XXVII (1985), pp. 1012–1020.

Lynne Rainen, "A membrane perfusion device for the production of monoclonal antibody" Amer. Biotech. Lab., 6(3):20–24 (Apr., 1988).

Nyberg, et al., Bilirubin Conjugation in a Three Compartment Hybrid Fiber Bioreactor, Annual International Conference of the IEEE Engineering in Medicine and Biology Society. vol. 12, No. 1, 1990 (pp. 443 & 444).

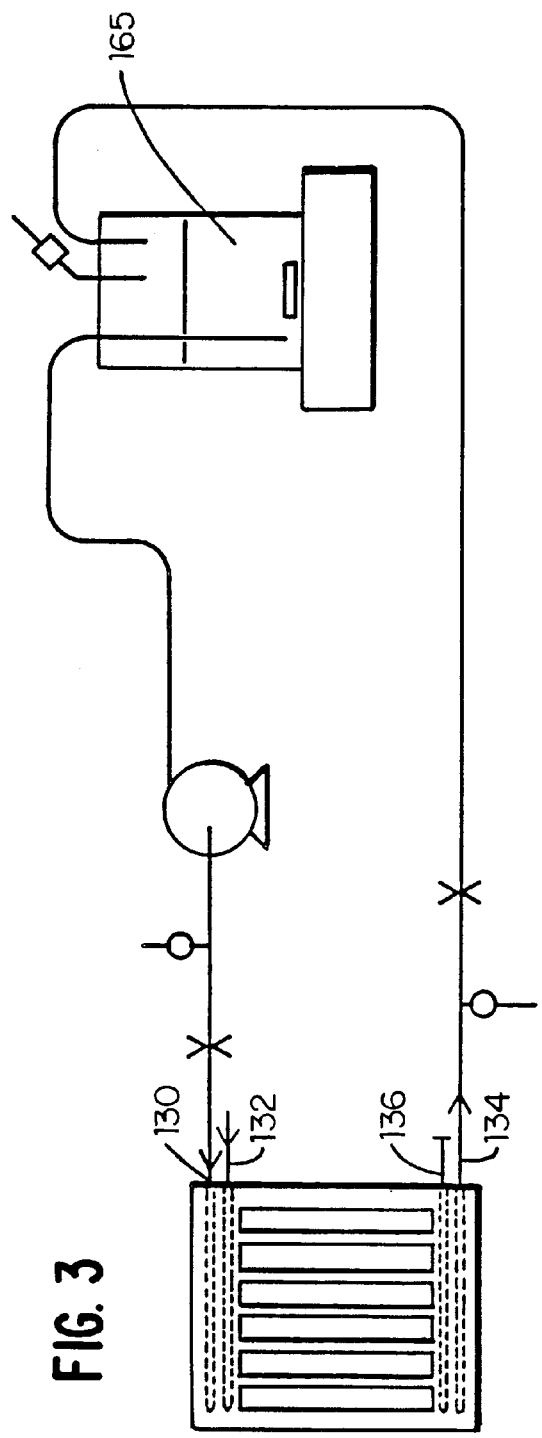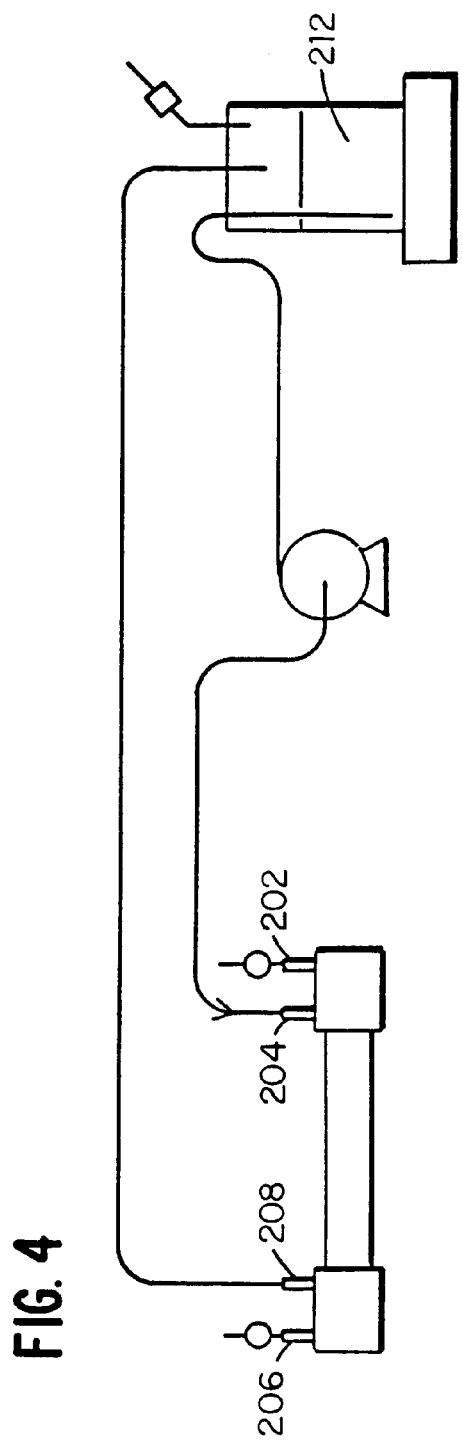

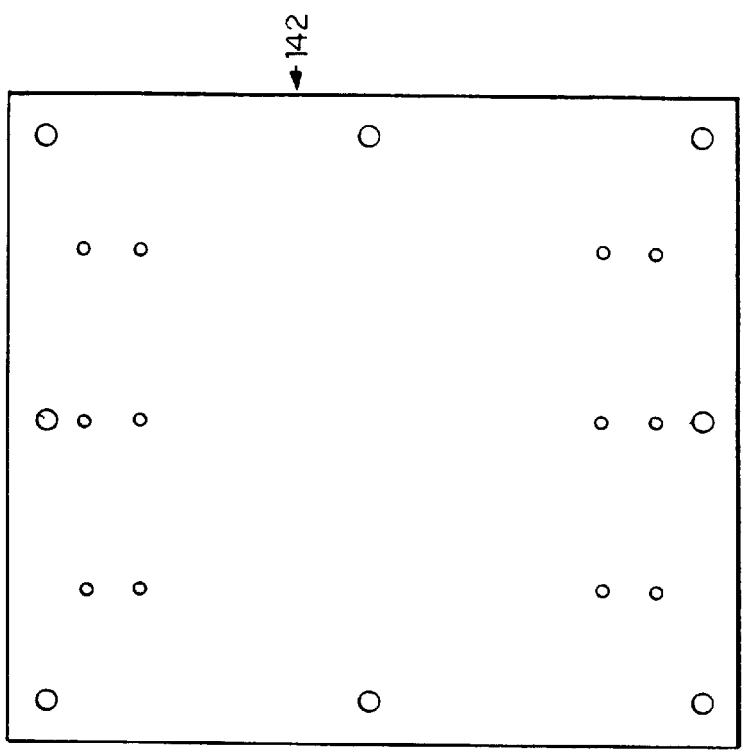
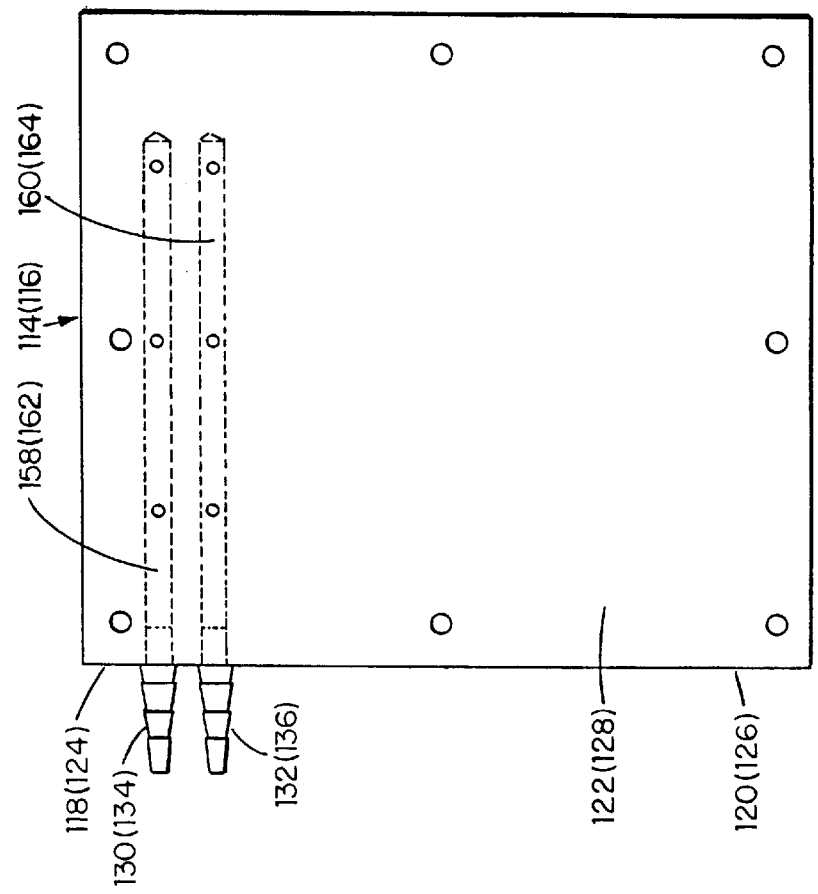

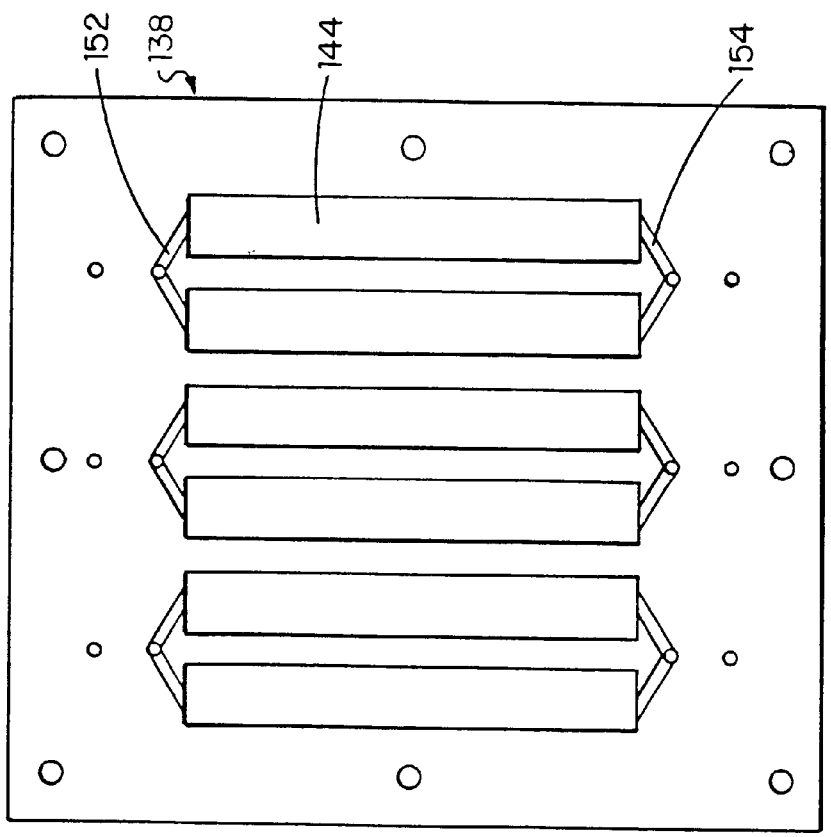
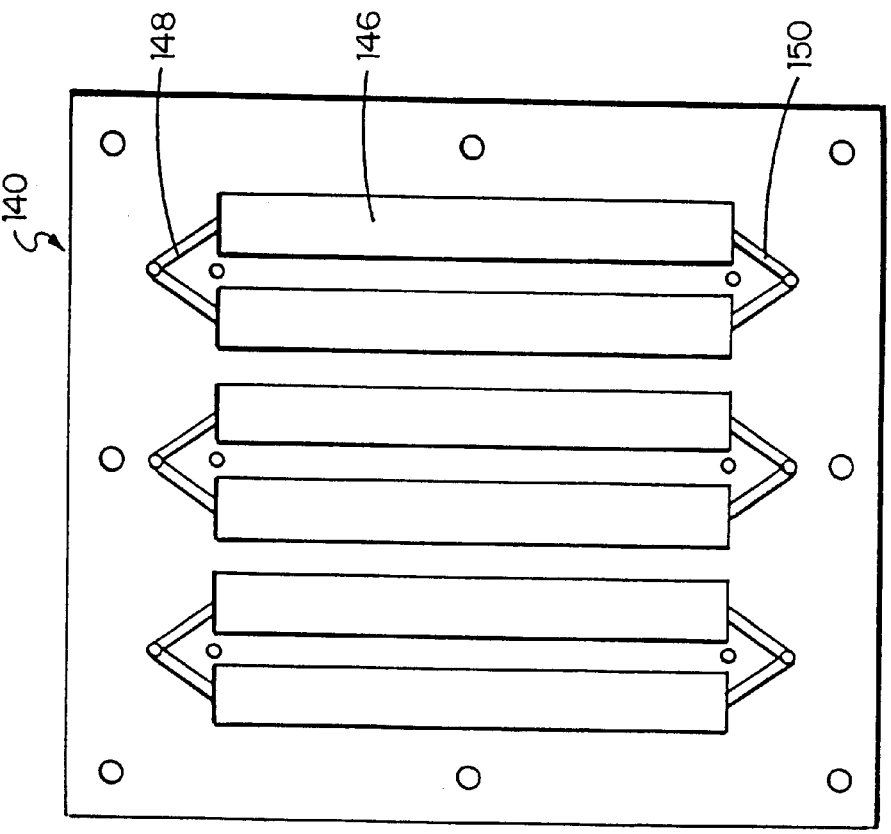
FIG. 9
FIG. 8

MAINTAINING CELLS FOR AN EXTENDED TIME BY ENTRAPMENT IN A CONTRACTED MATRIX

CROSS REFERENCE TO RELATED APPLICATIONS

This is a divisional of application Ser. No. 08/376,095 filed Jan. 20, 1995, now U.S. Pat. No. 5,605,835, which is a Continuation of application Ser. No. 07/864,893, filed Apr. 3, 1992, now abandoned, which is a continuation-in-part of application Ser. No. 07/355,115, filed May 18, 1989, now abandoned, which in turn is a continuation-in-part of application Ser. No. 07/197,700, filed May 23, 1988, now abandoned, and is a continuation-in-part of application Ser. No. 07/605,371, filed Oct. 29, 1990, now abandoned.

This invention was made with government support under NSF/BCS-8915307-01 awarded by the National Science Foundation. The government has certain rights in the invention.

FIELD OF THE INVENTION

This invention relates to an improved bioreactor apparatus for maintaining animal cells and genetically altered derivatives thereof in vitro in a viable and functioning state for extended periods of time. The invention involves the use of cells cultured in a three-dimensional gel matrix within a bioreactor such as a hollow-fiber or flat-bed system. In one embodiment, liver cells are maintained in a viable and functioning state in this bioreactor allowing this device to be used as a bioartificial liver for patients with liver failure. In other embodiments, genetically altered animal cells are maintained in a viable state and secreting molecular products, which are concentrated in the bioreactor, for extended periods of time.

BACKGROUND OF THE INVENTION

A. Bioreactor Device

Animal cells and genetically altered derivatives thereof are often cultivated in bioreactors for the continuous production of vaccines, monoclonal antibodies, and pharmaceutical proteins such as hormones, antigens, tissue type plasminogen activators, and the like. For example, pituitary cells can be cultured in vitro to produce growth hormones; kidney cells can be cultured to produce plasminogen activators; and cultured liver cells have been known to produce hepatitis A antigen. In these bioreactors, cells are essentially a system of catalysts and the medium supplies and removes the nutrients and growth inhibiting metabolites. To supply nutrients and remove metabolites, the medium in the bioreactor is changed either intermittently or continuously by fluid flow. However, because of their relatively small size and small density difference when compared to the medium, cells inevitably are withdrawn when the medium is changed, resulting in a relatively low cell concentration within the bioreactor. As a result of this low cell concentration, the concentration of the desired cell product is low in the harvested medium.

An ideal animal cell bioreactor would include three features:

(1) cells would be retained in a viable state at high densities in the bioreactor apparatus as long as possible, with an almost infinite residence time;

(2) high molecular weight compounds, including expensive growth factors and the desired cell products, would have a long but finite residence time within the bioreactor to allow for both efficient nutrient utilization by the growing cells and also the accumulation of cell products to a high concentration; and (3) low molecular weight compounds, including less expensive nutrients and inhibitory substances, should have a very short residence time within the bioreactor to reduce inhibition of cell growth, cell product formation, and other cellular metabolic activities.

Numerous procedures and devices for in vitro cell culture production of biomolecules have attempted to achieve these goals in the past. In relatively simple systems, the cells have been grown in tissue flasks and roller bottles in the presence of a suitable nutrient media. More complex systems have used capillary hollow fiber membranes as a surface support for the cells in conjunction with a means for supplying nutrient media to the cells.

For example, U.S. Pat. No. 4,537,860 to Tolbert describes a static cell culture maintenance system for maintaining animal cells in a substantially arrested state of proliferation with continuous secretion of cell product. The cells are retained within a reactor vessel chamber in a semi-rigid matrix having interstices for passage of fluid nutrient medium. Fresh nutrient medium is supplied by perfusion into the matrix through relatively low porosity tubes which are suspended in the reactor chamber and which substantially traverse the matrix. High porosity tubes are available to withdraw expended medium and cell product.

A membrane-type cell reactor is also shown in "Construction of a Large Scale Membrane Reactor System with Different Compartments for Cells, Medium and Product", Develop. Biol. Standard., Vol. 66, pages 221–226 (1987). In this membrane system, cells are immobilized in a wire matrix where different membranes separate the cells from the medium and the cells from the cell product. The membrane lying between the medium and the cells is an ultrafilter with a useful molecular weight cutoff preventing the particular cell product from crossing into the medium compartment. The other membrane is a microfiltration membrane which separates the cells from a cell product chamber. With this configuration it is possible to feed the cells continuously and harvest the collected cell product at a distinct time interval without removing cells.

While these reactor systems attempt to tackle the problems of maintaining a high cell concentration to consequently harvest a high level of cell product, there is much room for improvement. Accordingly, the bioreactor of the present invention provides an in vitro cell culture system which maintains a large number of cells for an almost infinite residence time with continuous or intermittent cell product secretion.

B. Bioartificial Liver

Most patients admitted to an intensive care unit in liver failure do not survive. (Shellman, R. G.; Fulkerson, W. J.; DeLong, E.; Piantadosi, C. A. "Prognosis of patients with cirrhosis and chronic liver disease admitted to the medical intensive care unit". Crit Care Med; July 1988; 16(7): 671–8.) Mortality as high as 80–90% has been reported. (Rueff, B.; Benhamou, J. P. "Acute hepatic necrosis and fulminant hepatic failure". GUT; 1983; 14: 805–15.) In 1987, more than twenty-six thousand people died of liver failure. Most of these deaths were not alcohol related. (Blake, J. E.; Compton, K. V.; Schmidt, W.; Orrego, H. "Accuracy of death certificates in the diagnosis of alcoholic liver cirrhosis". Alcoholism (N.Y.); February 1988; 12(1): 168–72.)

The patient in hepatic failure, unlike the patient in renal failure, cannot be specifically treated. Renal dialysis, which revolutionized the treatment of renal failure, does not presently have a hepatic equivalent. Currently, the only available treatment for refractory liver failure is hepatic transplantation. Many patients in hepatic failure do not qualify for transplantation due to concomitant infection, or other organ failure. Because of organ shortages and long waiting lists, even those who qualify for liver transplantation often die while awaiting an allograft. UCLA reported that one quarter of their transplant candidates died before a liver could be obtained. Organs suitable for transplant in the pediatric age group are even scarcer. (Busuttil, R. W.; Colonna J. O 2d; Hiatt, J. R.; Brems, J. J.; el Khoury G.; Goldstein, L. I.; Quinones-Baldrich, W. J.; Abdul-Rasool, I. H.; Ramming, K. P. "The first 100 liver transplants at UCLA". *Ann Surg*; October 1987; 206(4): 387–402.)

Multiple Organ Failure Syndrome remains a major cause of death in the surgical intensive care unit. Hepatic failure is believed to be the dominant dysfunction. However, these patients die with histologically normal livers—except for cholestasis. Many investigators believe that outcomes could be improved with short-term hepatic support; the liver, and the patient, would recover given time.

Currently, other organ systems can be externally supported: left ventricular assist devices exist for the injured heart; dialysis units are used for kidney failure; parenteral nutrition is used for the nonfunctioning gastrointestinal tract; ventilators, extracorporeal membrane oxygenators, and veno-venous bypass techniques are employed to support lung function. However, there is currently no substitute for the liver, either to "buy time" for liver recovery or to find a suitable organ for transplantation.

The development of an artificial liver is a complex problem. Many prior attempts, such as plasmapheresis, charcoal and resin hemoperfusion, and xenograft cross circulation, have failed. Unlike the heart, that has one major physiological function, the liver performs many complex tasks necessary for survival. These tasks have been difficult to develop or maintain in mechanical systems.

The liver is the metabolic factory required for the biotransformation of both endogenous and exogenous waste molecules and the synthesis of glucose, lipids, and proteins—including albumin, enzymes, clotting factors, and carrier molecules for trace elements. The liver maintains appropriate plasma concentrations of amino and fatty acids, as well as detoxifying nitrogenous wastes, drugs, and other chemicals. Waste products, such as bilirubin, are conjugated and excreted via the biliary tree. Hepatic protein synthesis and biotransformation vastly increase the complexity of hepatic support.

1. Culturing Hepatocytes

Systems that employ hepatocytes to provide biochemical function are problematic because hepatocytes can be difficult to maintain in culture. Under standard conditions, non-transformed hepatocytes cultured on plastic lose their gap junctions in about 12 to 24 hours; flatten, become agranular, and lose all their tissue specific functions in 3–5 days; and die within 1–2 weeks. (Reid, L. M.; Jefferson, D. M. "Culturing hepatocytes and other differentiated cells". *Hepatology*; May–June 1984; 4(3): 548–59; Warren, M.; Fry, Jr. "influence of medium composition on 7-alkoxycoumarin O-dealkylase activities of rat hepatocytes in primary maintenance culture". *Zenobiotica*; August 1988; 18(8): 973–81).

A solution to this problem is the use of transformed hepatocytes because they can be grown much more easily. However, transformed hepatocytes are often considered a poor choice because even well-differentiated transformed cells show marked variations in tissue specific function from their parent tissues. (Reid, et al., 1984, supra.) Moreover, many cell lines are transformed by viruses. (Aden, D. P.; Fogel, A.; Plotkin, S.; Damjanov, I.; Knowles, B. B. "Controlled synthesis of HBsAg in a differentiated human liver carcinoma-derived cell line". *Nature*, Dec. 6, 1979: 615–6; Knowles, B. B.; Howe, C. C.; Aden, D. P. "Human hepatocellular carcinoma cell lines secrete the major plasma proteins and hepatitis B surface antigen". *Science*; Jul. 25, 1980; 209: 497–9.) These cell lines have the potential to transmit the transforming virus to the patient. As a result, it is doubtful that regulatory agencies would approve the use of transformed cells for humans, even if the risk of transmission were proven minimal.

Many approaches to prolonging the viability and function of cultured hepatocytes and other differentiated cells have been investigated. These approaches have included adding hormones and growth factors to the culture media, adding extracellular matrix constituents, and growing the hepatocytes in the presence of another cell type. Cells routinely used in co-culture work with hepatocytes are endothelial cells, or hepatic nonparenchymal cells such as Kupffer cells.

2. Effect of Hormones and Growth Factors

The addition of corticosteroids to the incubation media has been shown to prolong survival of cultured hepatocytes and to maintain albumin synthesis—particularly in synergy with insulin. (Jefferson, D. M.; Clayton, D. F.; Darnell, J. E. Jr.; Reid, L. M. "Post-transcriptional modulation of gene expression in cultured rat hepatocytes". *Mol Cell Biol*, September 1984; 4(9): 1929–34; Dich, J.; Vind, C.; Grunnet, N. "Long-term culture of hepatocytes: effect of hormones on enzyme activities and metabolic capacity". *Hepatalogy*, January–February 1988; 8(1): 39–45.) DMSO (Dimethyl sulfoxide) and phenobarbital also are known to prolong hepatocyte viability and function. (Maher, J. J. "Primary hepatocyte culture: is it home away from home?" *Hepatology*; September–October 1988; 8(5): 1162–6.) Not all tissue specific functions are equally supported, however. Insulin can promote some functions with an effect that varies with concentration. If only insulin is added to the medium, urea cycle enzyme expression is decreased. This negative effect can be counteracted by the addition of glucagon and dexamethasone. (Dich, et al., 1988, supra.)

Hormonally defined media can also prolong hepatocyte function and viability. (Jefferson, et al., 1984, supra.) Using a serum-free hormonally defined medium, good function in baboon hepatocytes has been shown for over 70 days. This medium consisted of epidermal growth factor (100 ng/ml), insulin (10 $\mu$g/ml), glucagon (4 mg/ml), albumin (0.5 mg/ml), linoleic acid (5 mg/ml), hydrocortisone ($10^{-6}$ M), selenium ($10^{-7}$ M), cholera toxin (2 ng/ml), glycyl-histidyl-lysine (20 ng/ml), transferrin (5 mg/ml), ethanolamine ($10^{-6}$ M), prolactin (100 ng/ml), somatotropin (1 mg/ml), and thyrotropin releasing factor ($10^{-6}$ M). (Lanford, L. E.; Carey, K. D.; Estlack, L. E.; Smith, G. C.; Hay, R. V. "Analysis of plasma protein and lipoprotein synthesis in long-term primary cultures of baboon hepatocytes maintained in serum-free medium". *In Vitro Cell Dev Biol*, February 1989; 25(2): 174–82.) 3. Effect of Matrices It is now clear that the extracellular matrix has considerable influence on cell function and survival. (Bissell, M. J.; Aggeler, J. "Dynamic reciprocity: How do extracellular matrix and hormones direct gene expression". *Mechanisms of Signal Transduction by Hormones and Growth Factors*: Alan R. Liss, Inc.; 1987: 251–62.3.) Matrix elements have been shown to reduce or obviate the need for specific growth factors. Using extracted hepatic connective tissue, hepatocytes have been cultured for over 5 months and maintained albumin synthesis for at least 100 days. This extract represented approximately 1% of the liver by weight. One third of the extract was composed of carbohydrates and noncollagenous proteins; the other two thirds were collagens—43% Type 1, 43% Type III, and the remainder an undefined mixture of others including Type IV. (Rojkind, M.; Gatmaitan, Z.; Mackensen, S.; Giambrone, M.; Ponce, P.; Reid, L. "Connective tissue Biomatrix: Its Isolation and Utilization for Long-term Cultures of Normal Rat Hepatocytes". *J Cell Biol*, October 1980; 87: 255–63.) This mixture may not accurately reflect the local hepatocyte environment—the perisinusoidal space or Space of Disse.

The presence of matrix in the Space of Disse has been controversial. Some researchers initially suggested that the peri-sinusoidal space was "empty." It is now appreciated that all of the major constituents of basement membrane are present in or around the Space of Disse. (Bissell, D. M.; Choun, M. O. "The role of extracellular matrix in normal liver". *Scand. J. Gastroenterol.*; 1988; 23(suppl 151): 1–7.) Heparan sulfate proteoglycan binds both cell growth factors and cells. (Saksela, O.; Moscatelli, D.; Sommer, A.; Rifkin, D. B. "Endothelial cell-derived heparan sulfate binds basic fibroblast growth factor and protects it from proteolytic degradation". *J Cell Biol*, August 1988; 107(2): 743–51; Gordon, M. Y.; Riley, G. P.; Clarke, D.; "Heparan sulfate is necessary for adhesive interactions between human early hemopoietic progenitor cells and the extracellular matrix of the marrow microenvironment". *Leukemia* December 1988; 2(12): 804–9.) Heparan sulfate may directly effect the hepatocyte nucleus. (Ishihara, M.; Fedarko, N. S.; Conrad, H. E. "Transport of heparan sulfate into the nuclei of hepatocytes"; *J Biol Chem*; Oct 15, 1986; 261(29): 13575–80.) Hepatocytes secrete relatively abundant quantities of heparan sulfate in culture. (Arenson, D. M.; Friedman, S. L.; Bissell, D. M. "Formation of extracellular matrix in normal rat liver: lipocytes as a major source of proteoglycan". *Gastroenterology*, August 1988; 95(2): 441–7.) Immunological studies have identified Type I collagen, Type III collagen, Type IV collagen, fibronectin, and laminin in the Space of Disse. (Geerts, A.; Geuze, H. J.; Slot, J. W.; Voss, B.; Schuppan, D.; Schellinck, P.; Wisse, E. "Immunogold localization of procollagen III, fibronectin and heparan sulfate proteoglycan on ultrathin frozen sections of the normal rat liver". *Histochemistry;* 1986; 84(4–6): 355–62; Martinez-Hernandez, A. "The hepatic extracellular matrix. I. Electron immunohistochemical studies in normal rat liver". *Lab Invest*; July 1984; 51(1): 57–74.) There is normally little Type I collagen in the Space of Disse, although hepatocytes in culture show increasing Type I synthesis with de-differentiation. This is at the expense of Type III collagen synthesis. This effect is reversed with culture techniques that support tissue specific hepatocyte activity.

Hepatocytes also can be cultured on MATRIGEL™, a biomatrix produced by a sarcoma cell line (EHS). MATRIGEL contains Type IV collagen, laminin, entactin, and heparan sulfate. On MATRIGEL, hepatocytes have been shown to maintain normal albumin synthesis for 21 days. (Bissell, et al., 1987, supra.)

Close duplication of the normal environment of the hepatocyte has also been attempted by culturing hepatocytes in a confluent monolayer on collagen. A second layer of Type I collagen is added to recreate the normal matrix "sandwich" formed on the "top" and on the "bottom" of the hepatocyte. This technique has shown significantly improved viability and function with albumin synthesis for more than 42 days. (Dunn, J. C. Y.; Yarmush, M. L.; Koebe, H. G.; Tompkins, R. G. "Hepatocyte function and extracellular matrix geometry: long-term culture in a sandwich configuration". *FASEB*; February 1989; 3: 174–7.)

The effect of various proteoglycans and glycosaminoglycans on gap junction protein synthesis and genetic expression has also been carefully examined. The most effective compounds were dermatin sulfate proteoglycan, chondroitin sulfate proteoglycan, and heparan. Heparan extracted from the liver was most effective. Lambda carrageenan, a seaweed extract, was also effective. (Spray, D. C.; Fujita, M.; Saez, J. C.; Choi, H.; Watanabe, T.; Hertzberg, E.; Rosenberg, L. C.; Reid, L. M. "Proteoglycans and Glycosaminoglycans Induce Gap Junction Synthesis and Function in Primary Liver Cultures". *J Cell Biol* July 1987; 105: 541–55.) Finally, chitosan, a polysaccharide found in crustacean shells and fungal membranes, has been suggested as a factor that can mimic normal matrix and promote function and survival. (Muzzarelli, R.; Baldassarre, V.; Conti, F.; Ferrara, P.; Biagini, G.; Gazzanelli, G.; Vasi, V. "Biological activity of chitosan: ultrastructural study". *Biomaterials*; May 1988, 9(3): 247–52; Scholz, M. T.; Hu, W -S. "A two compartment cell entrapment bioreactor with three different holding times for cells, high and low molecular weight compounds". *Cytotechnology* 4: 127–137, 1990.)

4. Cell-Cell Co-Culture

Another successful technique for culturing differentiated liver cells involves co-culturing them with nonparenchymal cells. Recently, co-culture of hepatocytes on various endothelial lines was compared. Co-culture showed significantly improved albumin synthesis and maintenance of gap junctions. The cells were grown in the presence of insulin and dexamethasone. The addition of serum did not improve the results. The improved survival and function conferred by co-culture occurred only with cells in close proximity, and was not transferred by cell supernatants. (Goulet, F.; Normand, C.; Morin, O. "Cellular interactions promote tissue-specific function, biomatrix deposition and junctional communication of primary cultured hepatocytes". *Hepatology;* September–October 1988; 8(5): 1010–8.)

It is still controversial whether the beneficial effects of co-culture occur through matrix interactions or require cell-cell contact.

There is also evidence that lipocytes play a key role in matrix production. Lipocytes are reported to be as numerous as Kupffer cells, and have been suggested to produce the majority of Type I collagen, Type II collagen, Type IV collagen, laminin, and proteoglycans—particularly dermatin sulfate proteoglycan and chondroitin sulfate proteoglycan. (Friedman, S. L.; Roll, F. J.; Boyles, J.; Bissell, D. M. "Hepatic lipocytes: The principle collagen-producing cells of normal rat liver". *PNAS*; December 1985; 82: 8681–5.) It is of particular interest that these specific proteoglycans were those that best support gap junctions (Spray, et al., 1987, supra.).

5. Bioartificial Liver—Previous Investigations

Many techniques of artificial support have been utilized over the past three and a half decades. These include simple exchange transfusions (Lee, C.; Tink, A. "Exchange transfusion in hepatic coma: report of a case". *The Med. J. Australia*; Jan. 11, 1958: 40–42; Trey, C.; Burns, D. G.; Saunders, S. J. "Treatment of hepatic coma by exchange blood transfusion". *NEJM*; 1966; 274(9): 473–81); plasmapheresis with plasma exchange; (Sabin S, Merritt J A. "Treatment of hepatic coma in cirrhosis by plasmapheresis and plasma infusion [plasma exchange]". *Annals of Internal Medicine;* January 1968; 68(1): 1–6); extracorporeal heterologous or homologous liver perfusion (Eisemann, B.;

Liem, D. S.; Raffucci, F. "Heterologous liver perfusion in treatment of hepatic failure". *Annals of Surgery:* 1965; 162(3): 329–345; Sen, P. K.; Bhalerao, R. A.; Parulkar, G. P.; Samsi, A. B., Shah, B. K.; Kinare, S. G. "Use of isolated perfused cadaveric liver in the management of hepatic failure". *Surgery*; May 1966; 59(5): 774–781); cross-circulation (Burnell, J. M.; Dawlorn, J. K.; Epstein, R. B.; Gutman, R. A.; Leinbach, G. E.; Thomas, E. D.; Volwiler, W. "Acute hepatic coma treated by cross-circulation or exchange transfusions". *NEJM;* 1967; 276(17): 943–953); hemodialysis (Opolon, P.; Rapin, J. R.; Huguet, C.; Granger, A.; Delorme, M. L.; Boschat, M.; Sausse, A. "Hepatic failure coma (HFC) treated by polyacrylonitrile membrane (PAN) hemodialysis (HD)". *Trans. ASAIO,* 1976; 22: 701–710); activated charcoal hemoperfusion (Gazzard, B. G.; Weston, M. J.; Murray-Lyon, I. M.; Flax, H.; Record, C. O.; Portmann, B.; Langley, P. G.; Dunlop, E. H.; Mellon, P. J.; Ward, M. B.; Williams, R. "Charcoal haemoperfusion in the treatment of fulminant hepatic failure". *Lancet,* June 29; i: 1301–1307); and, more recently, bioartificial liver systems containing cultured hepatocytes.

Examples of bioartificial liver systems currently being investigated for support of liver failure include extracorporeal bioreactors (Arnaout, W. S.; Moscioni, A. D.; Barbour, R. L.; Demetriou, A. A. "Development of bioartificial liver: bilirubin conjugation in Gunn rats". *Journal of Surgical Research;* 1990; 48: 379–382; Margulis M S, Eruckhimov E. A.; Ahdieimann L. A.; Viksna L M. "Temporary organ substitution by hemoperfusion through suspense of active donor hepatocytes in a total complex of intensive therapy in patients with acute hepatic insufficiency". *Resuscitation;* 1989; 18: 85–94); and implantable hepatocyte cultures, such as microencapsulated gel droplets (Cai, Z.; Shi, Z.; O'Shea, G. M.; Sun, A. M. "Microencapsulated hepatocytes for bioartificial liver support". *Artificial Organs,*May 1988; 12(5): 388–393) and spheroid aggregates (Saito, S.; Sakagami, K.; Koide, N.; Morisaki, F.; Takasu S, Oiwa T, Orita K. "Transplantation of spheroidal aggregate cultured hepatocytes into rat spleen". *Transplantation Proceedings*; February 1989; 21(1): 2374–77). These bioartificial liver systems have the advantage of performing detoxification, synthesis and bioprocessing functions of the normal liver. Only a few extracorporeal bioreactors have been used in the clinical setting (Matsumura, K. N.; Guevara, G. R.; Huston, H.; Hamilto, W. L.; Rikimaru, M.; Yamasaki, G.; Matsumura, M. S. "Hybrid bioartificial liver in hepatic failure: preliminary clinical report". *Surgery,* January 1987; 101 (1): 99–103; Margulis, et al.; 1989, supra). Implantable hepatocyte cultures remain clinically untested.

The technique for hepatocyte entrapment within microencapsulated gel droplets (hepatocyte microencapsulation) is similar to the technique successfully used for pancreatic islet encapsulation (O'Shea, G. M.; Sun, A.M. "Encapsulation of rat islets of Langerhans prolongs xenograft survival in diabetic mice". *Diabetes*; August 1986; 35: 943–46; Cai, et al., 1988, supra). Microencapsulation allows nutrient diffusion to the hepatocytes, and metabolite and synthetic production diffusion from the hepatocytes. Microencapsulation also provides intraperitoneal hepatocytes with "immunoisolation" from the host defenses (Wong, H.; Chang, T. M. S. "The viability and regeneration of artificial cell microencapsulated rat hepatocyte xenograft transplants in mice". *Biomat. Art. Cells, Art. Org.*; 1988; 16(4): 731–739.) Plasma protein and albumin synthesis (Sun, A. M.; Cal, Z.; Shi, Z.; Fengzhu, M.; O'Shea, G. M.; Gharopetian, H. "Microencapsulated hepatocytes as a bioartificial liver". *Trans. ASAIO,* 1986; 32: 39–41; Cal, et al., 1988, supra); cytochrome P450 activity and conjugation activity (Tompkins, R. G.; Carter, E. A.; Carlson, J. D.; Yarmush, M. L. "Enzymatic function of alginate immobilized rate hepatocytes". *Biotechnol. Bioeng.;* 1988; 31: 11–18); gluconeogenesis (Miura, Y.; Akimoto, T.; Yagi, K. "Liver functions in hepatocytes entrapped within calcium alginate". *Ann. N.Y. Acad. Sci.*; 1988; 542: 531–32); ureagenesis (Sun, A. M.; Cal, Z.; Shi, Z.; Ma, F.; O'Shea, G. M. "Microencapsulated hepatocytes: an in vitro and in vivo study". *Biomat. Art. Cells, Art. Org.;* 1987; 15: 483–486); and hepatic stimulating substance production (Kashani, S. A.; Chang, T. M. S. "Release of hepatic stimulatory substance from cultures of free and microencapsulated hepatocytes: preliminary report". *Biomat., Art Cells, Art. Org.;* 1988; 16(4): 741–746) have all been reported by calcium alginate entrapped hepatocytes.

Spheroid aggregate cultured hepatocytes have also been proposed for the treatment of fulminant hepatic failure. Multiple techniques exist for hepatocyte aggregation into spheroids (Saito, S.; Sakagami, K.; Koide, N.; Morisaki, F.; Takasu, S.; Oiwa, T.; Orita, K. "Transplantation of spheroidal aggregate cultured hepatocytes into rat spleen". *Transplantation Proceedings*; February 1989; 21(1): 2374–77; Koide, N.; Shinji, T.; Tanube, T.; Asano, K.; Kawaguchi, M.; Sakaguchi, K.; Koide, Y.; Mori, M.; Tsuji, T. "Continued high albumin production by multicellular spheroids of adult rat hepatocytes formed in the presence of liver-derived proteoglycans". *Biochem. Biophys. Res. Comm.*; 1989; 161 (1): 385–91.) It is hypothesized that hepatocyte aggregation would improve the beneficial results of intraperitoneal hepatocyte injection therapy.

Extracorporeal bioreactor designs for the purpose of artificial liver support have included perfusion of small liver cubes (Lie T S, Jung V, Kachel F, Hohnke C, Lee K S. "Successful treatment of hepatic coma by a new artificial liver device in the pig". *Res. Exp. Med.;* 1985; 185: 483–494); dialysis against a hepatocyte suspension (Matsumura, et al., 1987, supra; Margulis, et al., 1989, supra); perfusion of multiple parallel plates (Uchino, J.; Tsuburaya, T.; Kumagai, F.; Hase, T.; Hamoda, T.; Komai, T.; Funatsu, A.; Hashimura, E.; Nakamura, K.; Kon, T. "A hybrid bioartificial liver composed of multiplated hepatocyte monolayers". *Trans. ASAIO;* 1988; 34:972–977); and hollow fiber perfusion. Human studies using extracorporeal hepatocyte suspensions have been reported.

The first clinical report of artificial liver support by dialysis against a hepatocyte suspension was released in 1987 (Matsumura, et al., 1987, supra). The device consisted of a rabbit hepatocyte liquid suspension (1–2 liters) separated from the patient's blood by a cellulose acetate dialysis membrane. Each treatment used fresh hepatocytes during a single four to six hour dialysis (run). Multiple runs successfully reduced serum bilirubin and reversed metabolic encephalopathy in a single case.

A controlled study from the USSR comparing dialysis against a hepatocyte suspension with standard medical therapy for support of acute liver failure was recently reported (Margulis, et al.; 1989, supra). The bioartificial device consisted of a small 20 ml cartridge filled with pig hepatocytes in liquid suspension, along with activated charcoal granules. The cartridge was perfused through a Scribner arteriovenous shunt access. Patients were treated daily for six hours. The hepatocyte suspension was changed hourly over each six hour treatment period. Improved survival was demonstrated in the treated group (63%) when compared with the standard medical therapy control group (41%).

Culturing hepatocytes with a hollow fiber cartridge is another example of bioartificial liver support. Traditionally, hepatocytes are loaded in the extracapillary space of the hollow fiber cartridge, while medium, blood or plasma is perfused through the lumen of the hollow fibers. Cells may be free in suspension (Wolf, C. F. W.; Munkelt, B. E. "Bilirubin conjugation by an artificial liver composed of cultured cells and synthetic capillaries". Trans. ASAIO; 1975; 21:16–27); attached to walls (Hager, J. C.; Carman, R.; Stoller, R.; Panol, G.; Leduc, E. H.; Thayer, W. R.; Porter, L. E.; Galletti, P. M.; Calabresi, P. "A Prototype For A Hybrid Artificial Liver". Trans. ASAIO; 1978; 24: 250–253); or attached to microcarriers which significantly increase the surface area within the extracapillary space (Arnaout, et al., 1990, supra).

Bilirubin uptake, conjugation and excretion by Reuber hepatoma cells within a hollow fiber cartridge was reported in 1975. (Wolf, et al., 1975, supra). Tumor cell suspensions were injected by syringe into the shell side of the compartment while bilirubin containing medium was perfused through the hollow fiber intraluminal space. This technique has not been reported clinically, possibly due to the risk of tumor seeding by hepatoma cells.

Another hollow fiber device developed for liver support uses hepatocytes attached to microcarriers loaded into the extracapillary cavity of a hollow fiber cartridge. In this device, blood flows through semi-permeable hollow fibers allowing the exchange of small molecules. Using this system, increased conjugated bilirubin levels have been measured in the bile of glucuronosyl transferase deficient (Gunn) rats. (Arnaout, W. S.; Mosicioni, A. D.; Barbour, R. L.; Demetriou, A. A. "Development of Bioartificial Liver: Bilirubin Conjugation in Gunn Rats". J. Surg. Research; 1990; 48: 379–82.) Since the outer shell is not perfused, all oxygen and nutrients are provided by the patient's blood stream. In addition, this system may require an intact in vivo biliary tree for the excretion of biliary and toxic wastes.

SUMMARY OF THE INVENTION

A. Bioreactor Device

In accordance with the bioreactor of the present invention, animal cells are maintained in vitro over a sustained period of time. Briefly, this bioreactor apparatus comprises two chambers, a feed and waste chamber and a cell chamber, separated by a selectively permeable membrane. This membrane selectively allows nutrients and cell waste products in the bioreactor apparatus to cross between the chambers but not the desired cell product. Within the cell chamber, a biocompatible, three-dimensional matrix entraps the animal cells. Due to the presence of this biocompatible matrix, the cell chamber generally has a gel phase, i.e., the biocompatible matrix, and a liquid phase containing a concentrated solution of the cell product to be harvested. Thus, the bioreactor of the present invention uses only two chambers to achieve three distinct zones within the bioreactor apparatus. Spent nutrients and cell waste products are withdrawn through an outlet means in flow communication with the feed and waste chamber. A withdrawal means, in flow communication with the cell chamber, may also be provided for collection of the desired cell product without disturbing the producing cells.

B. Bioartificial Liver

Furthermore, a hollow fiber bioreactor, in its "conventional" configuration, may not be optimal for a bioartificial liver. In a "conventional" hollow fiber configuration, such as the two described in the prior art discussed above, cells are loaded in the extracapillary cavity (shell) while the media flows through the lumen of the fibers. Potential problems exist in the extracapillary space such as uncontrolled fluid flow, fluid channelling, and location dependent cell concentration and viability. The present invention thus provides a new hollow fiber bioreactor configuration, as well as a new flat-bed configuration.

Accordingly, the present invention presents a novel bioreactor configuration for cell culture, which is particularly suitable for supporting viable hepatocytes in vitro. In one embodiment, this novel bioreactor is a hollow fiber cell culture bioreactor employing cells entrapped within a fibrous and highly porous collagenous gel matrix within the selectively permeable hollow fiber membrane lumen. In another embodiment, this novel bioreactor is a flat-bed bioreactor with cells entrapped within a matrix but separated from a media stream by a selectively permeable membrane.

This invention also relates to a cell gel matrix and a method of preparing such a cell gel matrix for cell cultivation. A bioartificial liver employing this novel bioreactor for supporting hepatocyte function in a patient suffering from hepatic failure is also provided by this invention. Tissue-specific function of other mammalian cells can also be supported using the cell gel matrix and the novel bioreactor provided by this invention. These and other advantages of the present invention will be further described herein.

Various features and advantages that result from a bioreactor apparatus and a bioartificial liver using the principles of this invention are pointed out with particularity in the claims. However, reference should also be made to the drawings and the accompanying detailed description of the invention for a more thorough understanding of the invention.

BRIEF DESCRIPTION OF THE DRAWINGS

FIG. 3 is a schematic view of a system using a flat bed type bioreactor apparatus;

FIG. 4 is a schematic view of a system using a hollow fiber bioreactor apparatus;

FIG. 6 is a plan view of a base plate used in the embodiment depicted in FIG. 5;

FIG. 7 is a plan view of a membrane used in the embodiment depicted in FIG. 5;

FIG. 8 is a plan view of a media plate used in the embodiment of the invention depicted in FIG. 5;

FIG. 9 is a plan view of a cell product plate used in the embodiment depicted in FIG. 5;

DETAILED DESCRIPTION OF THE INVENTION

A. Bioreactor Device

Figure 1:
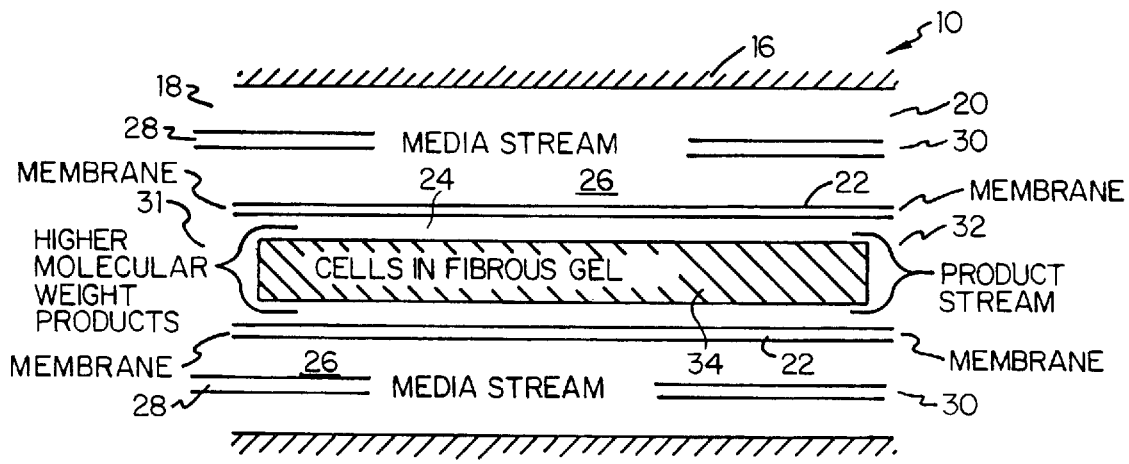
FIG. 1 is an abstract representation of a bioreactor apparatus that uses the inventive principles of the present invention.
Figure 2:
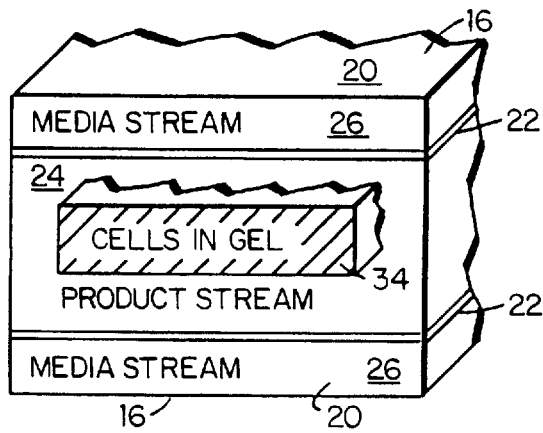
FIG. 2 is a pictorial representation of an embodiment of a bioreactor apparatus that uses the inventive principles of this disclosure.
Figure 5:
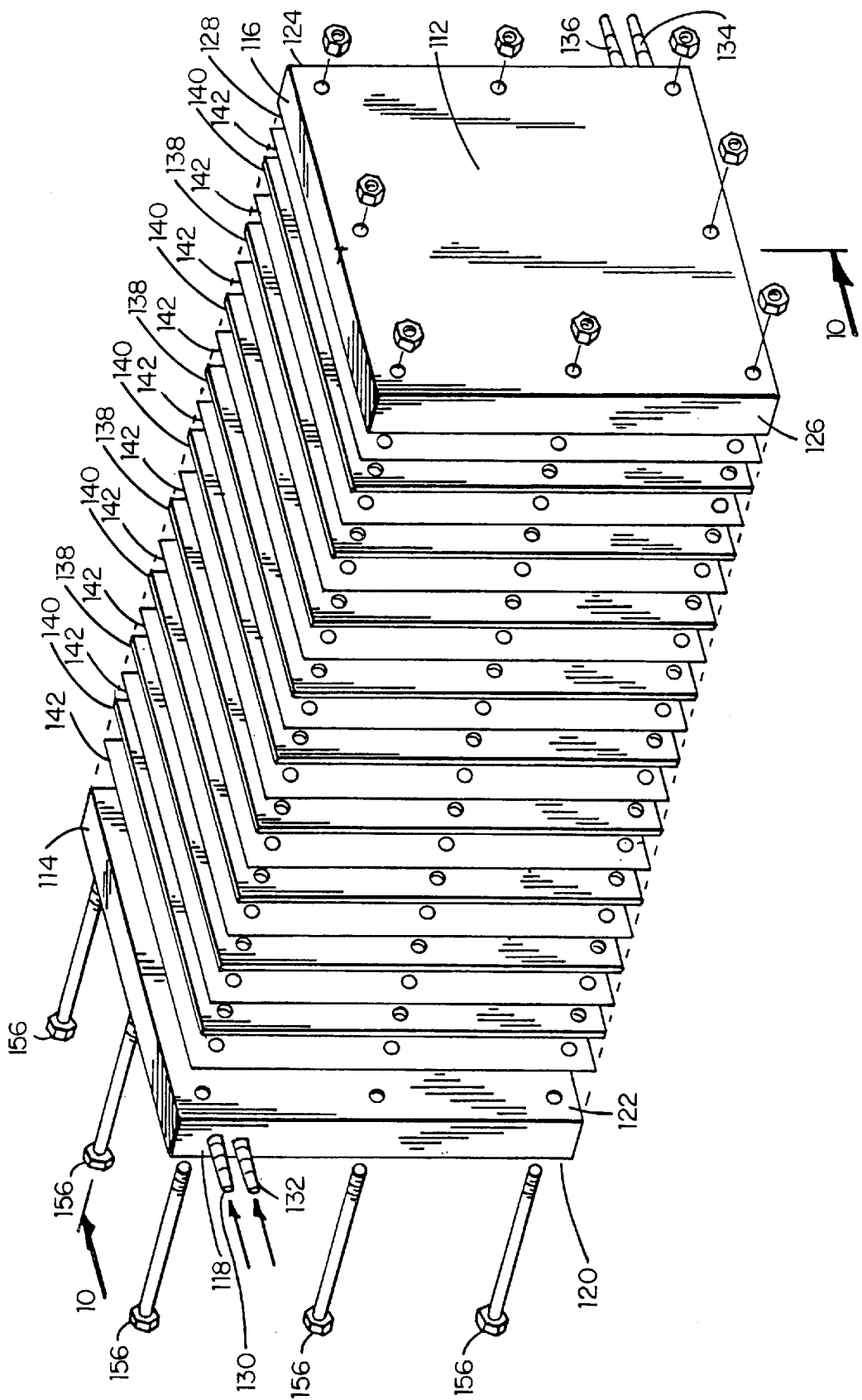
FIG. 5 is an exploded isometric view of an embodiment of the present invention.
Figure 10:
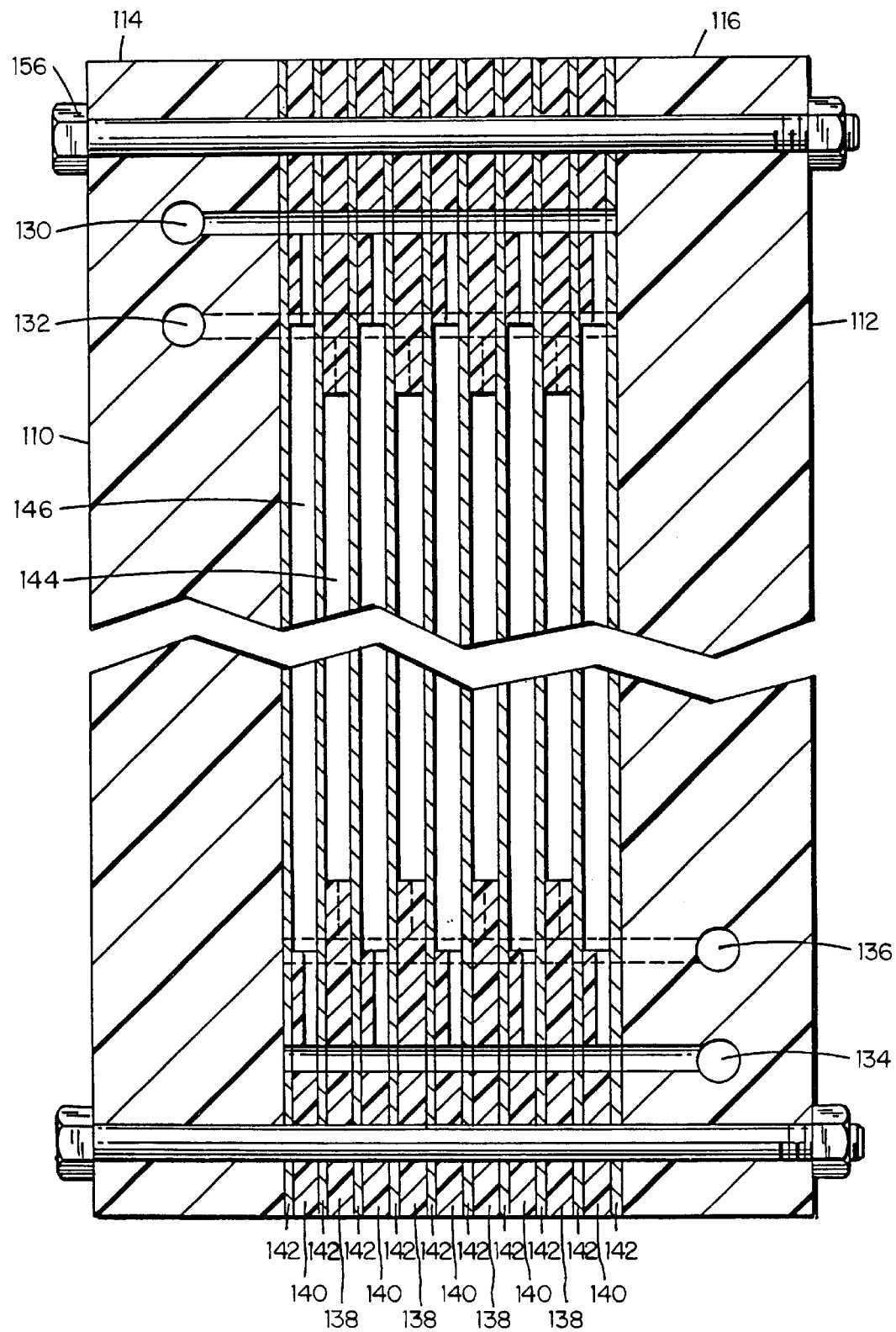
FIG. 10 is a cross-sectional view of the embodiment depicted in FIG. 5 through line 10—10.

With reference to the embodiment depicted in FIGS. 1 and 2, a bioreactor 10 according to the inventive principles of this disclosure would generally include two chambers within a housing means 16 having a proximal end 18 and distal end 20. A selectively permeable membrane 22 lies within housing means 16. Membrane 22 extends from proximal end 18 to distal end 20 to divide the interior of housing means 16 into a cell chamber 24 and a feed and waste chamber 26.

The preferred membrane selectively allows low molecular weight compounds, such as nutrients and cell waste products, to cross between cell chamber 24 and feed and waste chamber 26. However, membrane 22 does not allow high molecular weight compounds, such as the cell product to be harvested, to cross between the two chambers. The membrane must be permeable to essential nutrients and toxic waste products but must also retain the desired cell products in the cell chamber. Naturally, the desired upper molecular weight limit of the membrane will be chosen such that it is smaller than the molecular weight of the desired cell product. Thus, a suitable membrane for a cell product having a molecular weight exceeding 14,000 would be constructed of a processed cellulose having an upper molecular weight limit generally ranging from 12,000 to 14,000. Such a membrane is commercially available from Spectrum Medical Industries, Inc. of Los Angeles, Calif., under the trade name Spectra/Por 4. Other ultrafiltration membranes that could be used with a bioreactor system of the present invention include polysulfone, nylon, polypropylene, polyester/polycarbonate, TEFLON® (polytetrafluoroethylene), ionically charged membranes, Cellophane®, nitrocellulose, polyethylene and ceramics. A few commercial examples include polycarbonate and polyester NUCLEOPORE® membrane filters from Nucleopore Corporation in Pleasanton, Calif.; polysulfone PTGC membranes from Millipore of Bedford, Mass.; and nitrocellulose COLLODIUM® membrane filters from Schleicher and Schuell, Inc. in Keene, N.H.

Feed and waste chamber 26 supplies the cells with nutrient medium and carries away expended medium and cell waste products that have crossed membrane 22 to chamber 26. Inlet means 28 in flow communication with feed and waste chamber 26 is are provided for supplying the desired nutrient medium. Outlet means 30 further communicates with feed and waste chamber 26 to remove expended medium and cell waste products.

Growth or cell chamber 24 comprises two distinct phases: a substantially insoluble, biocompatible matrix 34 entrapping animal cells to form a gel phase; and a concentrated solution of the secreted cell product forming a liquid phase. The term insoluble as used herein refers to a composition which is capable of being separated from the cell culture medium by filtration. This bisectional cell chamber is formed when a suitable matrix precursor/cell suspension is placed within growth chamber 24. The cell containing matrix precursor suspension contracts within cell chamber 24 to form a generally dense, Insoluble, cell-biocompatible matrix 34. Utilizing biocompatible matrix 34, cells can be maintained in vitro for a very long period of time. Residence times of up to 90 days have been reached.

Generally, the cell-biocompatible matrix is formed when the chosen cells are mixed with a matrix precursor solution at lower temperatures (e.g., 0° C. to 30° C.), at lower pH values (e.g., 2 to 5.5), at both a lower temperature and a lower pH value, or in a solution of different ionic makeup. The chosen matrix precursor is preferably initially in a soluble form to create this cell suspension. The cell-matrix precursor suspension is then introduced into the cell chamber 24 through inlet means 31. When the pH, the temperature, or ionic character or polymer chain interaction is changed from the initial value, polymerization or aggregation occurs with the resulting polymer chains forming insoluble aggregates (e.g., pH value increased to the range of 6.8 to 7.4, temperature increased to the range of 37° C. to 45° C.). Generally, these insoluble aggregates will further aggregate to form fibers. These fibers, in turn, entrap the cells and the composition contracts creating what is referred to as the substantially insoluble, cell-biocompatible matrix 34.

It is further desired that the chosen matrix precursor have the ability to rapidly form a substantially insoluble, biocompatible matrix in situ uniformly entrap the cells, before the cells settle. The chosen matrix precursor should preferably form the fibrous matrix upon a physical or chemical change in the cell-matrix precursor suspension. Such a change could be the result of a shift in pH or temperature value, or both, addition of a comonomer or any other initiator of polymerization or cross-linking, or any combination of these methods. Depending on the chosen matrix precursor, the formed matrix could be the result of polymerization, aggregation, ionic complexation, hydrogen bonding or the like.

For the sake of convenience, it should be understood that wherever the term polymer or aggregate is used to refer to the matrix construction, the matrix is not limited to compounds with those characteristics. Any biocompatible, substantially insoluble matrix that forms in situ and entraps cells, at least initially, is considered to be within the scope of the present invention. Likewise, the matrix precursor should be read to include, but not be limited to, all compounds which tend to polymerize or aggregate or associate or the like to form the matrix in situ.

Due to contraction either caused by the cells or the matrix itself, the cell-biocompatible matrix will, in some cases, but not all, contract to one quarter of the original volume occupied by the mixture in a few hours or days. For the present invention it is not necessary for the cell-biocompatible matrix to contract to this extent. A cell-matrix which contracts to approximately 90% of the original volume occupied by the mixture is desired. A cell-matrix which has contracted to approximately 75% of the original volume occupied is even better. A cell-matrix which has contracted to approximately 50% of the original volume is even more preferred. However, the most desirable cell-matrix will contract to approximately one-third of the original volume occupied by the mixture.

After contraction has occurred, cell chamber 24 has two distinct zones, the cell-biocompatible matrix zone and a liquid zone in which high molecular weight compounds produced by the cells will accumulate. Cell products can be harvested periodically or continuously through withdrawal means 32.

The resulting matrix must be at least partially insoluble in the cell media that is employed under optimum culture conditions, e.g., pH=7.0–7.4; temperature=37° C.; and osmolarity=275–400 milliosmoles. In addition the cell-biocompatible matrix must be non-cytotoxic and sterilizable. Numerous matrix precursor compounds can be used to create the desired cell-biocompatible matrix.

One compound that has been found to form a particularly suitable matrix is collagen. Sterile, high purity native ateleopeptide collagen Type I is commercially available from Collagen Corporation in Palo Alto, Calif. under the trade name VITROGEN™ 100. Teleopeptide collagen Type I has also proven to be useful and is available in a relatively pure form from Gottefosse Corporation located in Elmsford, N.Y. under the trade name PANCOGENE S™. Whenever the term collagen is used in this description, it should be read to include any type of collagen or modified collagen which is at least partially insoluble under optimum cell culture conditions. For example, collagen may be modified according to the techniques of U.S. Pat. No. 4,559,304 to Kasai, et al., the disclosure of which is incorporated by reference herein.

A collagen-chitosan mixture may also be used. A suitable chitosan, which is a derivative of chitin in which many of the N-acetyl linkages have been hydrolysed to leave the free amine, can be obtained from Protan Labs of Redmond, Wash. in a dry state under the label Ultrapure Chitosan. As in the case of collagen, it should be recognized that the chitosan can also be chemically modified and still be an effective means for forming the matrix. In addition, the in situ polymerization of a fibrinogen and thrombin mixture to form fibrin has been successfully employed.

Other materials which would meet the requirements of this system include: (1) polyamines wherein the subunits which make up the polymer have a $pK_a$ value generally ranging from 7 to 10, such as collagen and chitosan. Such polyamines are soluble in a cell culture media at pH values generally in the range of 2 to 5.5 when in a protonated form and partially insoluble in a cell culture media at pH values generally ranging from 6.8 to 7.4 when in a partially unprotonated form; (2) a mixture of water soluble polyanionic polymers and polycationic polymers. This mixture would associate through ionic bonds and fall out of solution; and (3) polymers, such as cellulose ethers, which are soluble in a cell culture media temperatures ranging from 0° C. to 30° C. but insoluble in a cell culture media at higher temperatures, such as those generally ranging from 32° C. to 45° C. have also been contemplated.

These principles were incorporated in a flat bed type embodiment 100 of the present invention as shown in FIGS. 5 through 10. The external housing of flat bed bioreactor 100 is formed by exterior faces 110 and 112 of a first base plate 114 and a second base plate 116. FIG. 6 shows base plates 114 and 116 in more detail. Base plates 114, 116 are preferably made of polycarbonate because it is transparent and steam sterilizable. However, base plates 114 and 116 could be constructed of any suitable synthetic resin or metal. First base plate 114 has proximal 118 and distal 120 ends and exterior 110 and interior faces 122. Second base plate 116 has proximal 124 and distal 126 ends and exterior 112 and interior faces 128. First base plate 114 has first 130 and second 132 fluid inlet means.

Both fluid inlet means 130, 132 are preferably located near the proximal end 118 of first base plate 114, with second fluid inlet means 132 located slightly posterior to or below first fluid inlet means 130. Second base plate 116 has first 134 and second fluid outlet means 136. Both fluid outlet means are located near distal end 126 of second base plate 11 6, preferably with second fluid outlet means 136 slightly anterior to or above first fluid outlet means 134. Second fluid outlet means 136 and second fluid inlet means 132 may be capped with a rubber septum or equipped with a short piece of tubing terminated in a valve if only periodic harvesting of cell product is desired.

Between interior faces 122, 118 of first base plate 114 and second base plates 116 are alternating cell growth plate(s) 138, selectively permeable membranes 142 and nutrient medium plate(s) 140. Bioreactor 100 has at least one cell growth media plate 138 as shown more particularly in FIG. 9. Each cell growth plate 138 has at least one longitudinal window 144. The length of the cell growth plate window(s) 144 is substantially equal to the distance from second fluid inlet means 132 to second fluid outlet means 136 as measured in the assembled flat bed bioreactor 100.

As shown more particularly in FIG. 8, bioreactor 100 also has at least one nutrient medium plate 140. Each nutrient medium plate 140 has at least one longitudinal window 146. The length of nutrient medium plate window(s) 146 is substantially equal to the distance from first fluid inlet means 130 to first fluid outlet means 134 as measured in the assembled flat bed bioreactor 100. Thus, the length of nutrient medium plate window(s) 146 is slightly longer than the length of cell plate window(s) 144. Naturally, the length of longitudinal windows 144, 146 depends upon the location of first and second fluid inlet and outlet means 134, 136. Thus, it is possible that window 144 may be slightly longer than the length of nutrient medium window(s) 146. In this case the length of the nutrient medium window(s) 144 will be substantially equal to the distance from the first fluid inlet means 130 to the first fluid outlet means 134, as measured in the assembled flat bed bioreactor 100, and the length of the call plate window(s) 146 will be substantially equal to the distance from the second fluid inlet means 132 to the second fluid outlet means 136.

In the preferred embodiment, at least one first medium channel(s) 148 is in flow communication with first fluid inlet means 130 and nutrient medium plate window(s) 146. At least one second medium channel(s) 150 is in flow communication with nutrient medium plate window(s) 146 and first fluid outlet means 136. At least one first cell channel(s) 152 is in flow communication with second fluid inlet means 132 and cell growth plate window(s) 144. At least one second cell channel(s) 154 is in flow communication with cell growth plate window(s) 144 and second fluid outlet means 136. Channels 148, 150, 152, and 154 do not extend through their respective plate 138, 140. On first base plate 114, in flow communication with first and second fluid inlet means 130, 132 and channels 148, 152 are preferably first and second fluid inlet flow manifolds 158, 160. Likewise, first and second fluid outlet flow manifolds 162, 164 on second base plate 116 are in flow communication with first and second fluid outlet means 134, 136 and channels 150, 154. Preferably, the bore size of manifolds 160, 164 are small to avoid dilution of the product stream as the product is withdrawn.

Selectively permeable membranes 142 as shown in FIG. 7 and used in flat bed bioreactor 100 of this invention are pervious to the passage of nutrients and cell waste products from one side of membrane 142 to the other, while being substantially impervious to the passage of the animal cells and desired cell products from one side of membrane 142 to the other.

Base plates 114, 116, plates 138, 140 and membranes 142 are preferably assembled together in the following sandwich-type fashion to form flat plate bioreactor 100 of the present invention. Exterior faces 110, 112 of first 114 and second base plates 116 are positioned with each face outward from each other, forming the exterior housing of bioreactor 100. Plates 138, 140 and membranes 142 are sandwiched between base plates 114, 116, so that nutrient medium plate(s) 140 alternates with cell growth plate(s) 138, while each membrane 142 separates each plate from each other plate and from interior face 122, 128 of each base plate 114, 116. Securing means 156, such as bolts, screws, clamps or the like can be used to hold the assembled sandwich bioreactor apparatus.

It is not necessary for operation of bioreactor 100 that membrane 142 be placed between base plates 114, 116 and medium plate(s) 138, 140. However, when used in this fashion, the membranes serve as an effective gasket. In forming the sandwich structure of bioreactor 100 the first and last plate of the sandwich, excluding base plates 114, 116, is preferably a nutrient medium plate 140. Preferably, a flat bed bioreactor 100 of this invention is formed with a plurality of cell growth plates 138 and nutrient medium plates 140 and a plurality of membranes 142.

In operation, the chosen cell nutrient media is pumped with a peristaltic pump, as shown in FIG. 3, from a media reservoir 165 through first fluid inlet means 130 and first medium channel(s) 148 to nutrient medium plate window(s) 146. A suitable pump is a variable speed Masterflex Cat. No. 7533-30 with size 16 Masterflex silicone tubing from Cole Palmer in Chicago, Ill. Medium continues through nutrient medium plate window(s) 146 to second medium channel(s) 150 and subsequently out of flat bed bioreactor 100 through first fluid outlet means 134. The cell-matrix precursor suspension is introduced through second fluid inlet means 132, through first cell channel(s) 152 into cell growth plate window(s) 144. Second fluid outlet means 136 is preferably capped.

After the cell-matrix precursor suspension is introduced into cell growth plate window(s) 144, the cell entrapping, substantially insoluble matrix 34 is formed in situ. Cells are maintained by the continuous flow of nutrient medium which crosses membrane 142. Toxic cell waste products diffuse across membrane 142 to nutrient medium plate window(s) 146, where they are carried out of bioreactor 100. Due to their high molecular weights, cell products to be harvested do not cross membrane 142.

To periodically harvest the cell products, a syringe, or other withdrawing means may be inserted into second fluid outlet means 136. For continuous harvesting, either a pump or a sample flow control valve may be employed. Alternatively, fluid may be introduced into the cell chamber, displacing the cell products to be harvested.

Figure 11:
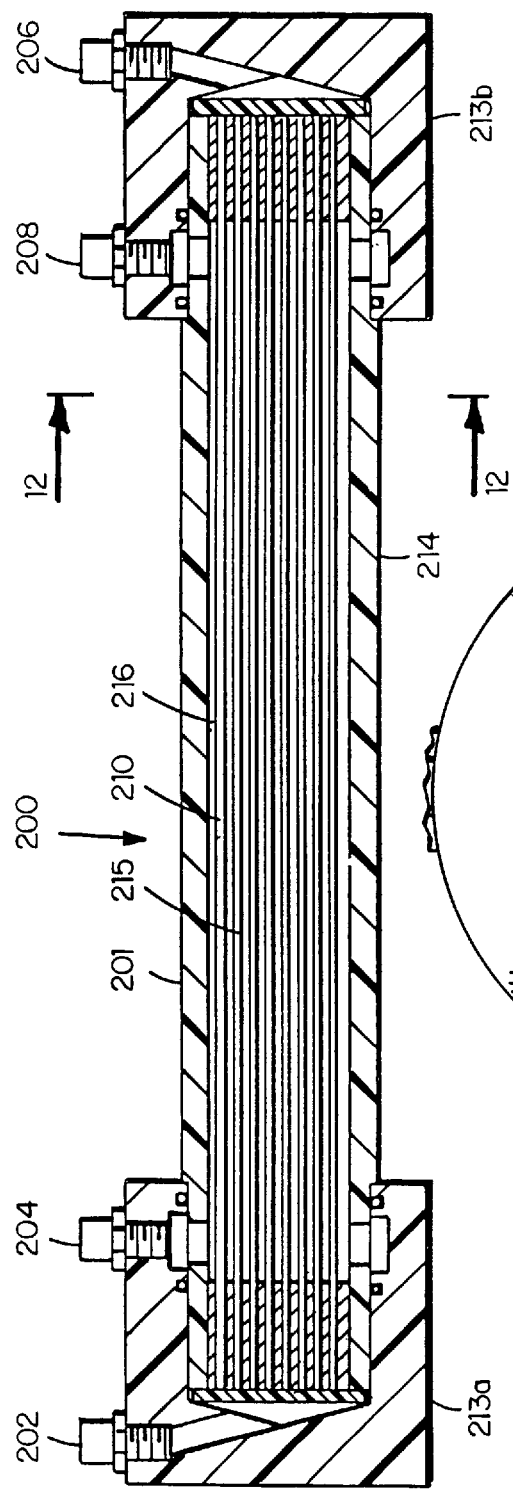
FIG. 11 is a side cross-sectional view of another embodiment of the present invention.
Figure 12:
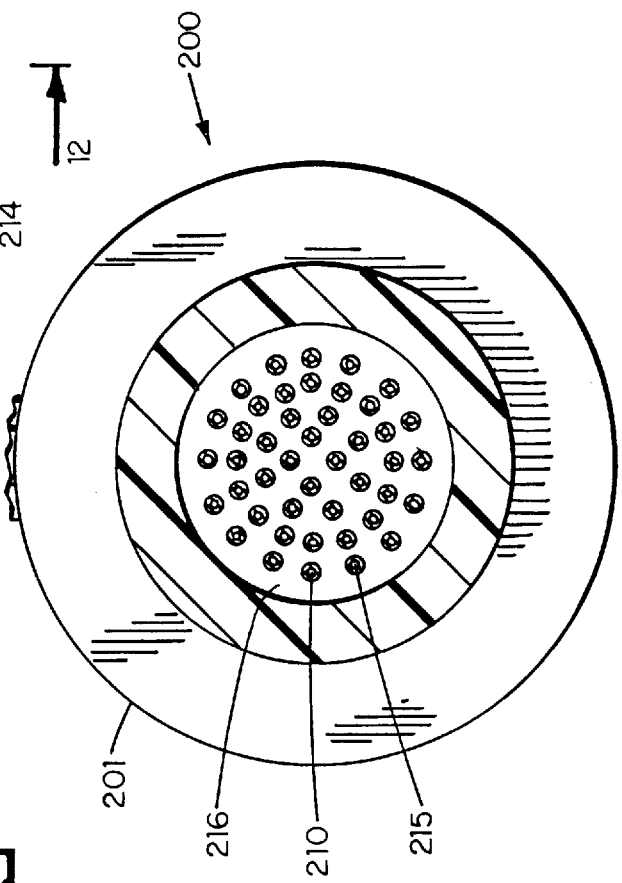
FIG. 12 is a cross-sectional view of the embodiment depicted in FIG. 11 through line 12—12.

Alternatively, the principles of the present invention can be employed in a hollow fiber bioreactor 200 as shown in FIGS. 11 and 12. A suitable hollow fiber assembly is the Amicon PN 5407 Model DH4 from Amicon, a division of W. R. Grace & Co. in Danvers, Mass., with the pressure control valve and filter frits removed. An Amicon H1P30-43 hollow fiber membrane assembly having an upper molecular weight limit of approximately 30,000 was used. The hollow fibers of this assembly were formed of polysulfone, although any suitable membrane composition as discussed above may also be successfully employed.

A suitable hollow-fiber assembly 200 has a housing 201 having spaced end portions 213a, 213b defining a chamber 214 therebetween. Housing 201 has a first 202 and second 204 fluid inlet means with second fluid inlet means 204 positioned generally toward the inside of first fluid inlet means 202. Housing 201 also has a first 206 and second 208 fluid outlet means, with second fluid outlet means 208 positioned generally toward the inside of first fluid outlet means 206. While housing 201 is depicted in FIGS. 11 and 12 as being cylindrical, its shape is not so limited. Any housing may be successfully employed which will house hollow fibers.

Within housing 201 is at least one selectively permeable hollow fiber 210, pervious to the passage of nutrients and toxic cell waste products while substantially impervious to the passage of cells and the desired cell product, extending the length of housing 201. Hollow fiber 210 divides chamber 214 into an intracapillary space 215 within hollow fiber 210 and an extracapillary space 216 outside hollow fiber 210. Intracapillary space 215 and extracapillary space 216 communicate only through the walls of hollow fiber 210. Preferably, intracapillary space 215 provides a cell chamber for cells entrapped in the chosen matrix while extracapillary space 216 provides a nutrient medium, or feed and waste chamber. These roles may be reversed, if desired. Preferably, a plurality of fibers would be employed. The interior lumens of hollow fibers 210 are in flow communication with first fluid inlet means 202 and first fluid outlet means 206. Extracapillary space 216 is in flow communication with second fluid inlet means 204 and second fluid outlet means 208.

In operation, as shown in FIG. 4, nutrient medium would be pumped from reservoir 212 through second fluid inlet means 204, if extracapillary space 216 is to be used as the nutrient medium or feed and waste chamber. The medium travels through extracapillary space 216 and exits housing 201 through second fluid outlet means 208. The matrix precursor-cell suspension is introduced into hollow fibers 210 through first fluid inlet means 202, if intracapillary space 215 is to be used as the cell chamber. First fluid outlet means 206 is capped with a rubber septum or a short piece of tubing terminated in a valve. The substantially insoluble, cell-matrix subsequently forms in situ within hollow fibers 210.

Nutrient medium crosses the semi-permeable membrane wall of hollow fiber 210 to feed the entrapped cells. Cell waste products and expended medium perfuse through the walls of hollow fibers 210 into the extracapillary space where they are carried away with the medium stream. The desired cell product can be harvested continuously or periodically through first fluid outlet means 206.

Figure 22:
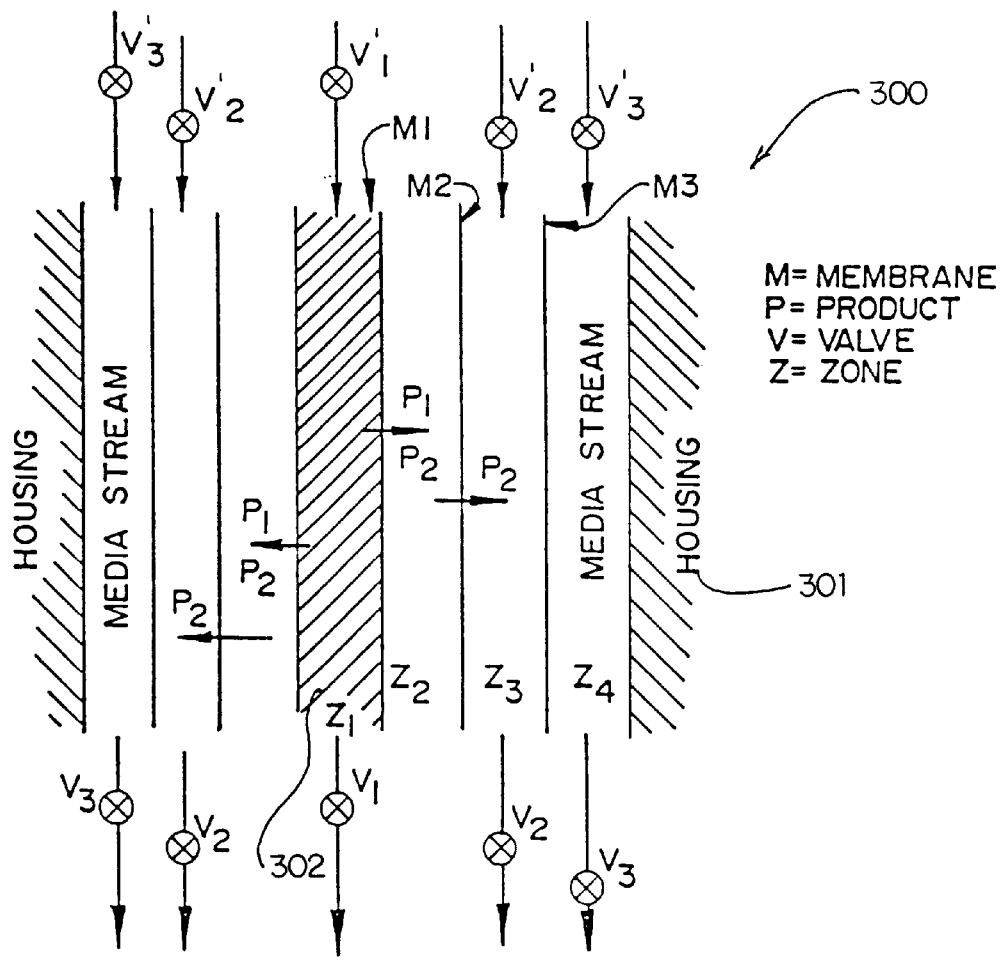
FIG. 22 is an abstract representation of a bioreactor apparatus that uses the inventive principles of the present invention.
Figure 23:
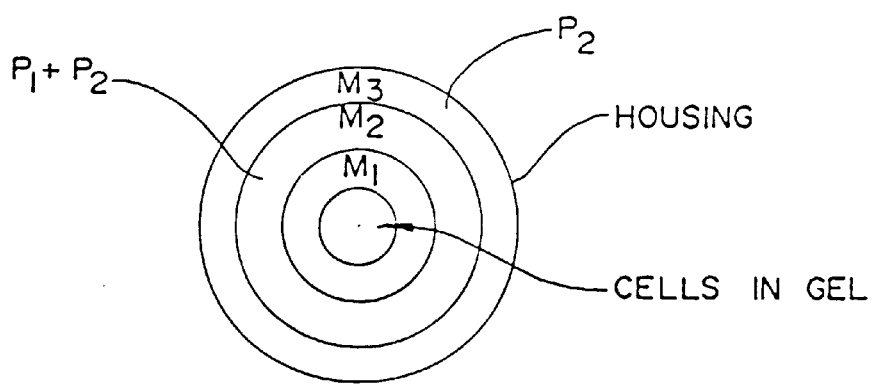
FIG. 23 is a cross-sectional view of the embodiment depicted in FIG. 22.

A multizone bioreactor design could also employ the principles of the present invention. This bioreactor configuration would be particularly useful where harvesting of more than one cell product is desired. In this configuration, the cell products to be harvested, $P_1$ and $P_2$, would have significantly different molecular weights. For example, cell product $P_1$ would have a molecular weight that is significantly greater than that of cell product $P_2$. As shown in FIGS. 22 and 23, a multizone bioreactor according to the principles of the present invention, generally referred to as 300, would consist of multiple concentric, selectively permeable hollow fibers $M_1$, $M_2$, and $M_3$ of different pore sizes sealed in a housing 301 having spaced end portions and defining a chamber therebetween.

As depicted in FIG. 22, within the housing chamber of multizone bioreactor 300 would be a first selectively permeable hollow fiber $M_1$ which would be preferably pervious to the passage of nutrients, toxic cell waste products and cell products $P_1$ and $P_2$ while substantially impervious to the passage of cells. Within the intracapillary space of first hollow fiber $M_1$ is a first zone $Z_1$. A second selectively permeable hollow fiber $M_2$ would be concentric to said first hollow fiber $M_1$. Second hollow fiber $M_2$ would preferably be substantially pervious to the passage of nutrients and cell waste products while impervious to at least one cell product e.g., $P_1$. Second hollow fiber $M_2$ creates a second zone $Z_2$ within the intracapillary space intermediate first hollow fiber $M_1$ and second hollow fiber $M_2$.

A third selectively permeable hollow fiber $M_3$ would be concentric to second hollow fiber $M_2$. Third hollow fiber $M_3$ would preferably be substantially pervious to the passage of nutrients and cell waste products while impervious to the passage of all desired cell products, here, $P_1$ and $P_2$. Third hollow fiber $M_3$ creates two additional zones: a third zone $Z_3$ is created in the intracapillary space intermediate second hollow fiber $M_2$ and third hollow fiber $M_3$ while a fourth zone $Z_4$ is created within the extracapillary space intermediate third hollow fiber $M_3$ and housing 301.

With this configuration, first hollow fiber $M_1$, second hollow fiber $M_2$ and third hollow fiber $M_3$ would allow nutrients and cell waste products to cross from zone $Z_1$ to zone $Z_4$ and from zone $Z_4$ to zone $Z_1$. However, cell product $P_1$ would be contained within zone $Z_2$. Cell product $P_2$, on the other hand, would be able to freely diffuse through second hollow fiber $M_2$ into zone $Z_3$. The pore size of third hollow fiber $M_3$, however, would prevent cell product $P_2$ from diffusing into zone $Z_4$. It should be understood, however, that greater than or less than four zones may be possible, depending upon the number of cell products to be harvested and the desired concentration. The embodiment shown in FIGS. 22 and 23 is not intended to be a definitive representation of a multizone bioreactor.

A suitable, commercially available concentric hollow fiber bioreactor for use with the present invention is available from Setec, Inc. of Livermore, Calif. under the trademark TRICENTRIC®. The hollow fibers of this assembly are formed of polypropylene, although any suitable membrane composition discussed above may also be successfully employed.

In operation, a suitable matrix precursor/cell solution would be introduced into zone $Z_1$ through valve means $V_1'$, which would be in flow communication with zone $Z_1$, where the suspension subsequently contracts to form a generally dense, insoluble cell—biocompatible matrix 302. Matrix 302, and cell products, can be removed through valve means $V_1$ which is also in flow communication with zone $Z_1$. With matrix 302, cells can be maintained in vitro for a very long period of time.

Nutrient media is passed by means of valve means $V_3$ and $V_3'$ through zone $Z_4$. Valve means $V_3$ and $V_3'$ are in flow communication with zone $Z_4$. The low molecular weight nutrients freely diffuse through hollow fibers $M_1$, $M_2$ and $M_3$ to maintain the cells residing in zone $Z_1$. Similarly, low molecular weight cell waste products and inhibitory metabolites are able to diffuse through the series of concentric hollow fibers into zone $Z_4$. The media stream in zone $Z_4$ carries away expended nutrient medium and cell waste products from the assembly.

The residence times of cell products $P_1$ and $P_2$ are controlled by the operator. These products can be harvested either continuously or intermittently through valve means in flow communication with the desired zone. As depicted in FIG. 22, the cell product stream from zone $Z_2$ would contain both cell products $P_1$ and $P_2$ whereas that of zone $Z_3$ would contain only cell product $P_2$. Cell product $P_2$ could be readily removed from zone $Z_3$ through use of valve means $V_2$ and $V_2'$.

If a relatively pure stream of $P_1$ was desired, on the other hand, valve means $V_1'$, $V_2$ and $V_2'$ could be opened and valve means $V_1$, $V_3$ and $V_3'$ closed while nutrient medium is pumped into zone $Z_1$ through valve means $V_1$. In this manner, nutrient medium would be forced to diffuse through second hollow fiber $M_2$, carrying residual cell product $P_2$ with it, and out of the assembly through valve means $V_2$. Since cell product $P_1$ cannot pass through hollow fiber $M_2$, in this configuration, cell product $P_1$ would remain in zone $Z_2$ and could be subsequently harvested. This method would result in some dilution of cell product $P_2$ but the stream of cell product $P_2$ would still be several times more concentrated than if the cells were grown in conventional bioreactor systems.

Other designs may also be employed. The essential design feature of a bioreactor apparatus of the present invention is the use of at least two chambers to achieve at least three distinct zones within the bioreactor by incorporating an in situ forming matrix.

A bioreactor apparatus using the principles of the present invention provides high oxygen transfer to the entrapped cells to maintain cell viability within the bioreactor with a low shear flow. Moreover, because of the concentrated cell product that is withdrawn, cell product recovery costs are reduced. Indeed, in many cases a substantially cell free cell product is achieved. A bioreactor apparatus according to the principles of the present invention may also be used to harvest nonsurface dependent cells such as AFP-27. These cells eventually slough off the matrix due to cell multiplication and can be harvested along with the desired cell product.

Figure 20:
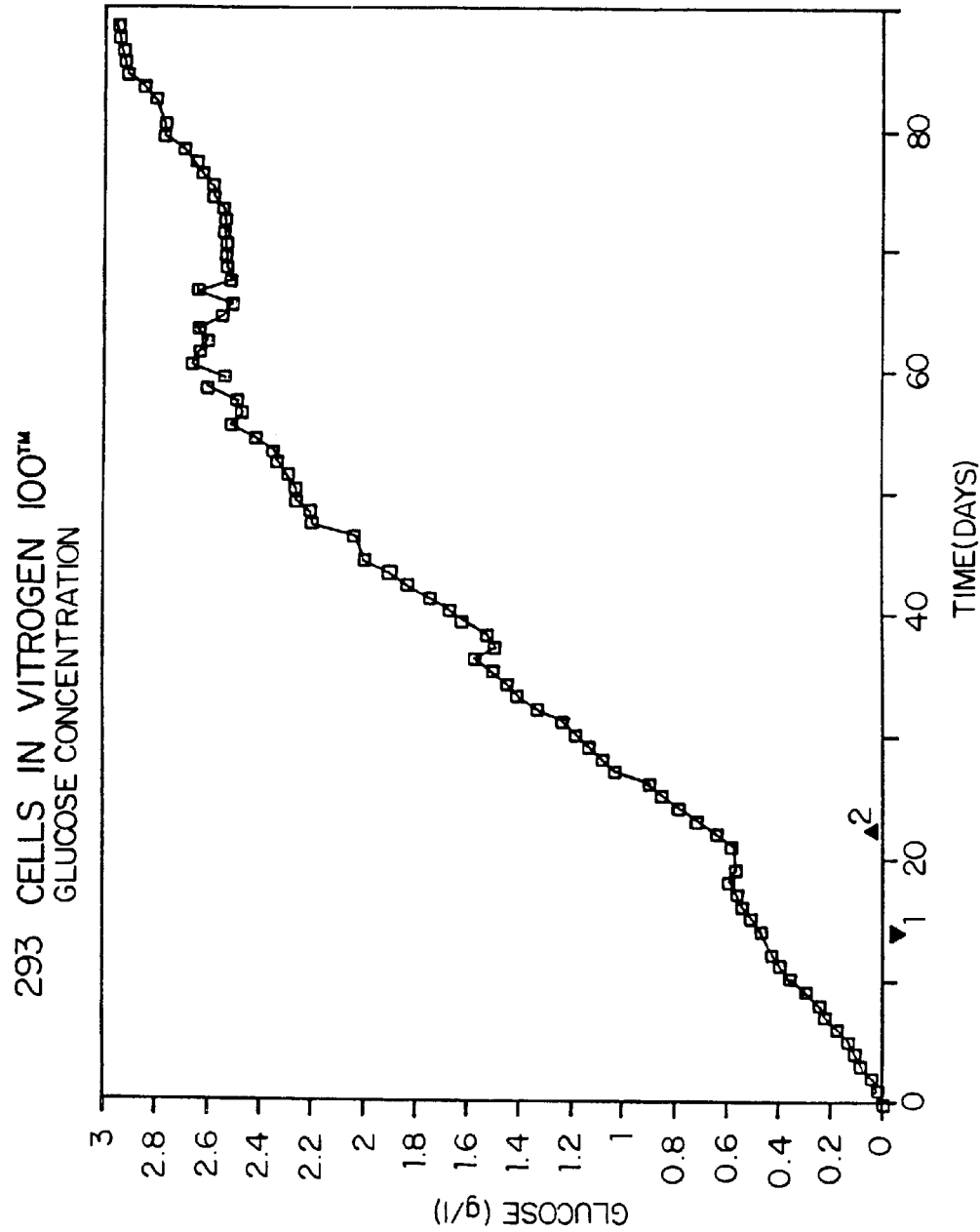
FIG. 20 is a graph.

The results further demonstrate that rapid start-up of this bioreactor apparatus is possible as well as step changes from serum containing medium to serum free medium and in many cases even protein free medium as shown in Example 6. A "step change" means to change instantaneously rather than gradually. In the context of this application, step change refers to the removal of medium containing serum entirely from the medium reservoirs 165, 212 and the feed and waste chamber and the subsequent replacement with serum free medium. As shown by the triangles in FIG. 20, after serum free medium is introduced into the bioreactor in a step change fashion, rather than a gradual or prolonged transition period, the cells remain viable. Triangle 2 indicates that time when serum free medium was introduced into the system. The rapid change to a serum free medium did not result in a decreased glucose consumption rate or cell death as usually occurs in other devices. By allowing for the rapid introduction of serum free medium, the bioreactor apparatus of the present invention can be set up and operated quickly and efficiently.

The following examples will more fully illustrate how animal cells and their genetically altered derivatives can be cast into a substantially insoluble biocompatible matrix. The resulting cellular response in these systems is also described.

EXAMPLE 1

293 Cells in a Collagen Matrix

In a laminar flow HEPA filtered hood, two sterile 15 ml screw-cap tubes, Tube A and Tube B, were prepared for use.

To Tube A, 1.75 ml of modified Dulbecco's Modification of Eagles Medium (DME) was added. This medium had previously been prepared to twice the normal concentration and which included 10% fetal bovine serum (FBS); 300 μg/ml geneticen, 200 μg/ml hygromycin B, and 2 μg/ml Vitamin K. The resulting medium mixture was sterilized by filtration. 0.10 ml of steam sterilized 0.1 N NaOH as added to Tube A. 1.0 ml of sterile VITROGEN 100™ was added to Tube B. Both tubes were sealed and placed in an ice water bath to cool the solutions to generally less than 4° C.

Genetically engineered human kidney epithelial cells ("293 cells") were used for this example. The base cells are publicly available under Deposit No. CRL 1573 at the ATCC in Rockville, Md. Using standard and well known techniques, these cells can be genetically manipulated so that the cells produce Protein C, a natural anticoagulant protein. See, e.g., Lawrence H. Clouse, and Philip C. Comp., "The Regulation of Hemostasis: The Protein C System", *NEJM* 314(20), 1298 (May 15, 1986); P. C. Comp, and L. H. Clouse, "Plasma Proteins C and S: The Function and Assay of Two Natural Anticoagulants", *Laboratory Management*, pp. 29–32 (December 1985).

The 293 cells were grown to confluence in a 75 cm$^2$ tissue culture flask in a solution of DME, which included 5% FBS; 600 μg/ml geneticin; 400 μg/ml hygromycin B; and 2 μg/ml vitamin K ("DME+Ab solution") according to standard tissue culture techniques. See, eg., R. Ian Freshney, Alan R. Liss, *Culture of Animal Cells, A Manual of Basic Technique*, (1983). Using aseptic techniques, the medium was removed from the flask and the cells were gently washed with 5.0 ml of phosphate buffered saline (PBS) solution to remove residual serum. The PBS solution contained 8 g/l sodium chloride, 0.2 g/l potassium chloride, 2.0 g/l sodium phosphate dibasic and 0.40 g/l potassium phosphate monobasic. The PBS solution was then removed.

1.0 ml of a 0.25% Trypsin solution in PBS was subsequently added. The cells and solution were incubated for 5 minutes at 37° C. After the incubation period, a solution of DME+Ab was added to inactivate the trypsin. Cells were sloughed off the surface and suspended in the added medium.

Again using aseptic techniques, the contents of Tube A were added to the contents of Tube B. Immediately following this addition step, 0.9 ml of the cell suspension (6.15× 10$^7$ total cells) was added to Tube B. The contents of Tube B were then mixed well by inverting the tube several times. The resulting mixture was poured into a 34 mm tissue culture dish and incubated at 37° C. to form a substantially insoluble cell-biocompatible matrix. The amount of matrix contraction was measured daily using the methods described in Bell et al, "Production of a Tissue-Like Structure by Contraction of Collagen Lattices by Human Fibroblasts of Different Proliferative Potential In Vitro", *PNAS:* USA, Vol. 76, No. 3 pp. 1274–1278 (March 1979).

3.0 ml of the liquid medium was removed and replaced daily without disturbing the cell laden matrix. Glucose concentration was measured in the removed medium using a Sigma Diagnostic Glucose HK hexokinase enzymatic assay available from Sigma-Aldrich Co. In St. Louis, Mo. Using standard ELISA assay techniques, the concentration of Protein C was also determined.

Figure 13:
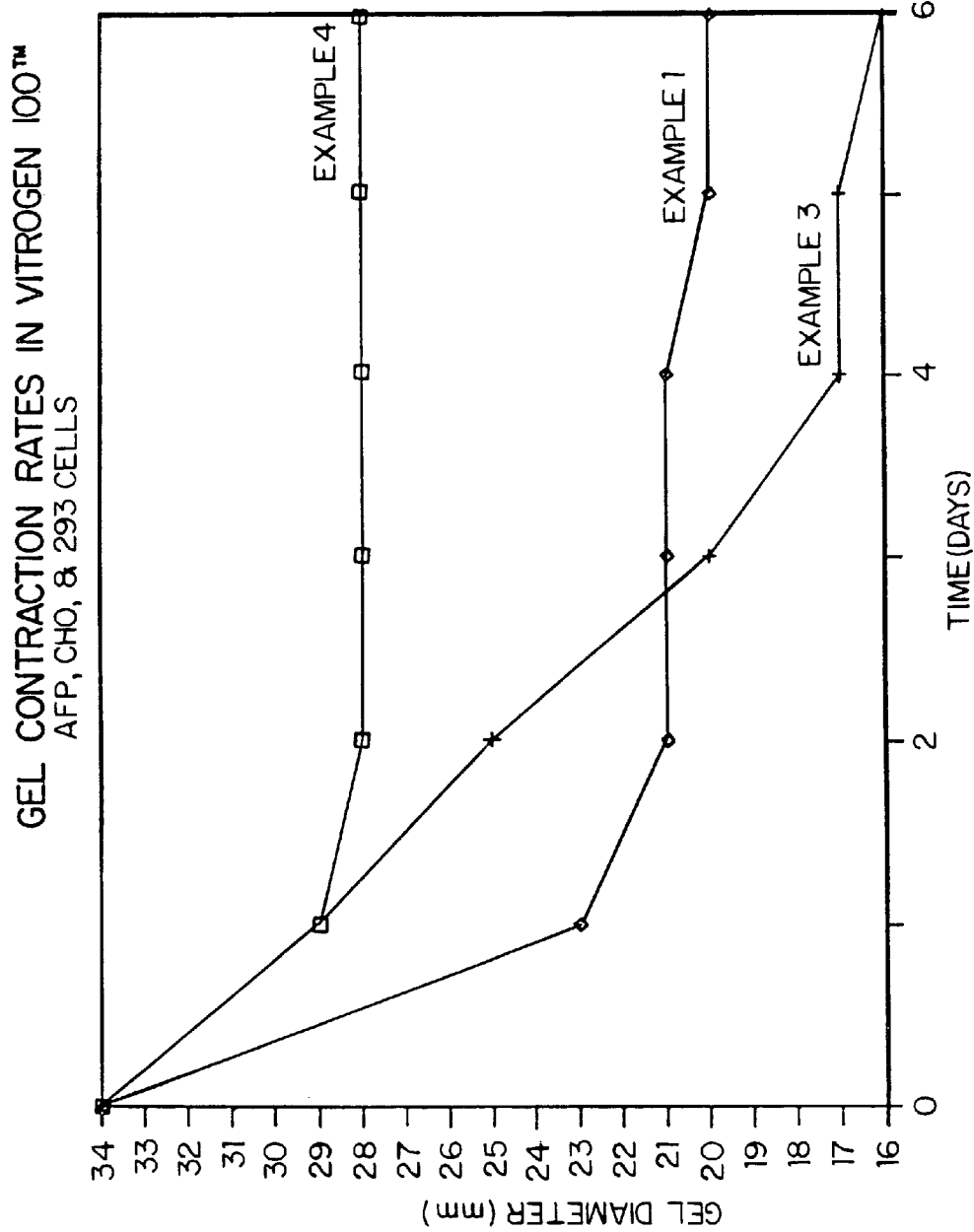
FIG. 13 is a graph.
Figure 14:
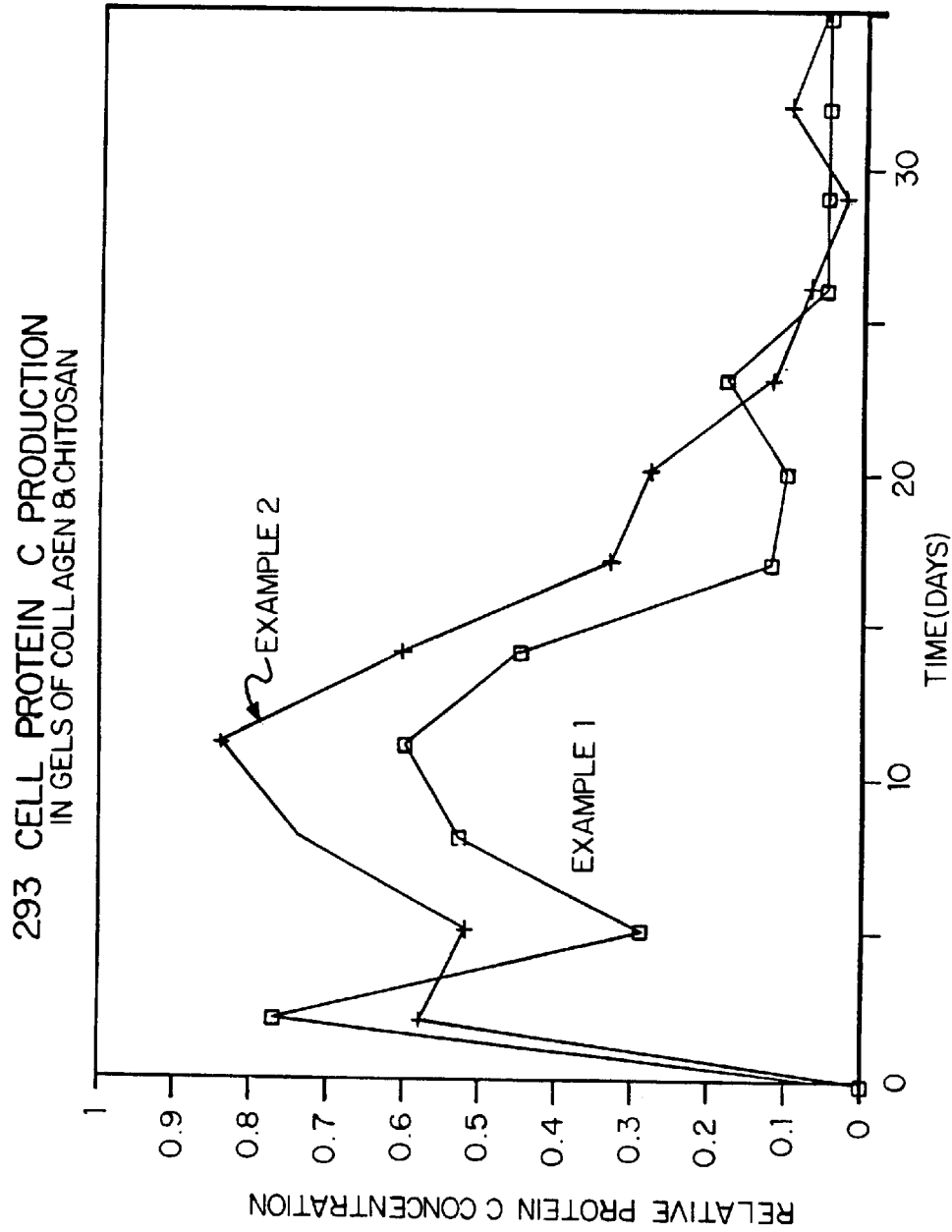
FIG. 14 is a graph.

FIG. 13 shows the rate of matrix contraction by comparing the gel diameter against time. After an initially high rate of contraction, the diameter of the cell matrix was generally stable. FIG. 14 represents the concentration of Protein C that was contained in the spent medium. The glucose uptake curve of FIG. 15 verifies the continued viability of the cells after being incorporated in the polymer matrix.

EXAMPLE 2

293 Cells in a Collagen—Chitosan Matrix

Figure 15:
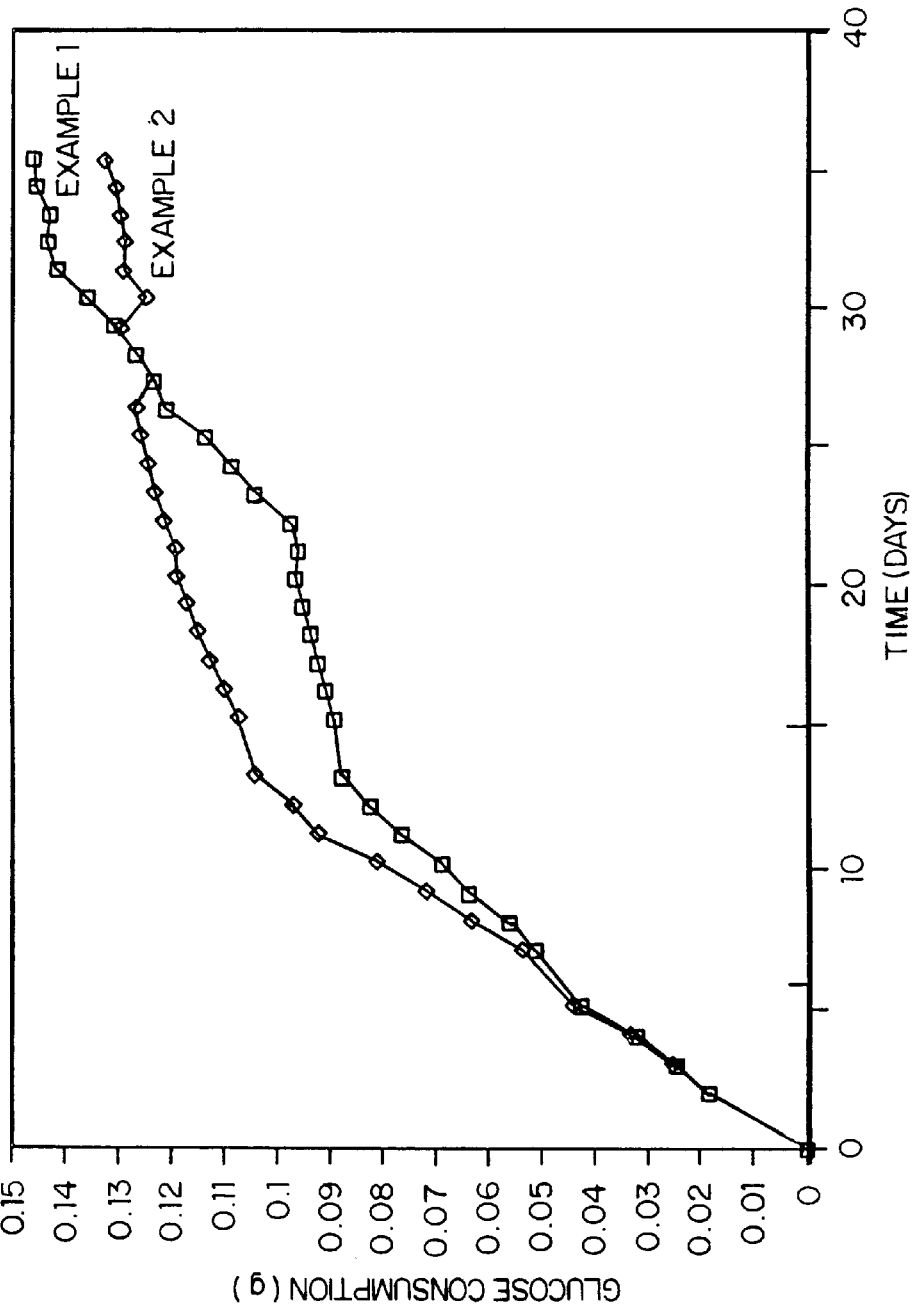
FIG. 15 is a graph.

For this example the procedure of Example 1 was used except that Tube B further included 0.5 ml of a 2% aqueous solution of chiotsan, prepared by dissolving Ultrapure Chitosan (Protan Labs, Lot No. PTL-173) in distilled water, steam sterilized at 121° C. for 30 minutes and then adjusted to pH 4. In the resulting solution the collagen concentration was reduced to 0.1% mg/ml. Using this mixture in Tube B a chitosan-collagen-cell matrix was created. FIG. 14 demonstrates the successful production of Protein C over a prolonged period of time when the cells were incorporated in the biocompatible matrix. As shown in FIG. 15, the cells continued to consume glucose while entrapped in this matrix.

EXAMPLE 3

Chinese Hamster Ovary Cells in a Collagen Matrix

The protocol of Example 1 was modified to test the cell growth and contraction of Chinese Hamster Ovary Cells (CHO) in a collagen matrix. In this example Tube A held 1.05 ml of a double concentration of DME, containing 10% by volume FBS; 200 units/ml penicillin G; 200 μg/ml streptomycin; and 0.06 ml of 0.1 N sodium hydroxide.

The CHO cells were prepared for use according to standard and well known techniques, e.g., V. B. Himes and W. S. Hu, "Attachment and Growth of Mammalian Cells on Microcarriers with Different Ion Exchange Capacities", supra. The cells were subsequently suspended in a DME solution having 5% by volume FBS. 37.5 ml of a hamster cell suspension (7×10$^5$ cells/ml) was centrifuged. Medium was removed until only 3 ml of medium remained, increasing the hamster cell concentration to 8.75×10$^6$ cells/ml.

1.5 ml of the CHO cell suspension (1.31×10$^7$ total cells) was added to the mixed contents of Tubes A and B. The mixture was then poured into a petri dish as explained in Example 1. However, rather than incubating the petri dish, the dish was floated on a 37° C. water bath. In this way, the contents were rapidly warmed and fibrillogenesis of the collagen was forced to occur before the cells settled. After the substantially insoluble cell matrix formed, 5.0 ml of DME with 5% FBS and 100 units/ml Penicillin G and 100 μg/ml Streptomycin was gently added to the surface of the cell matrix gel. Approximately 7.0 ml of medium was changed on a daily basis.

Figure 16:
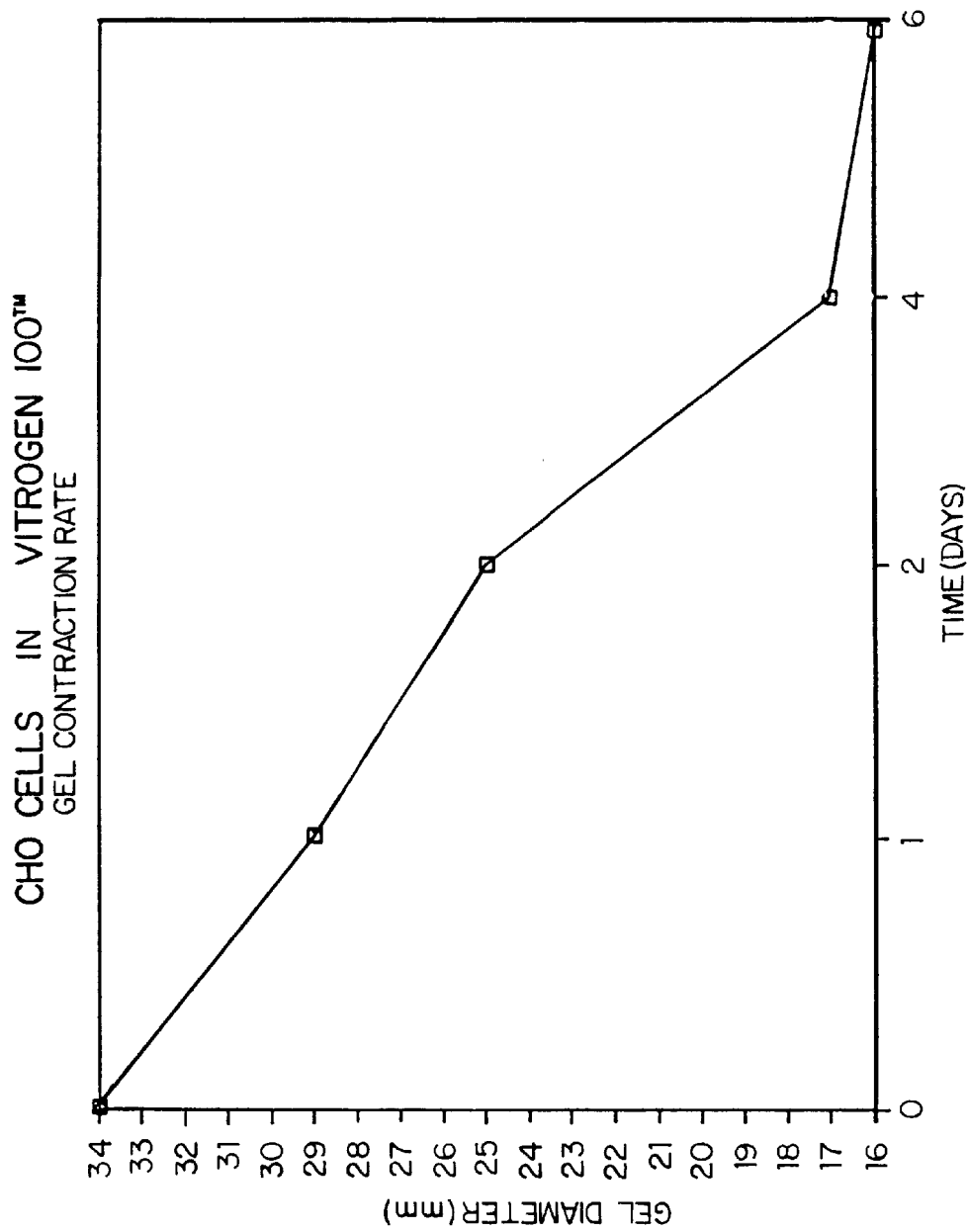
FIG. 16 is a graph.
Figure 17:
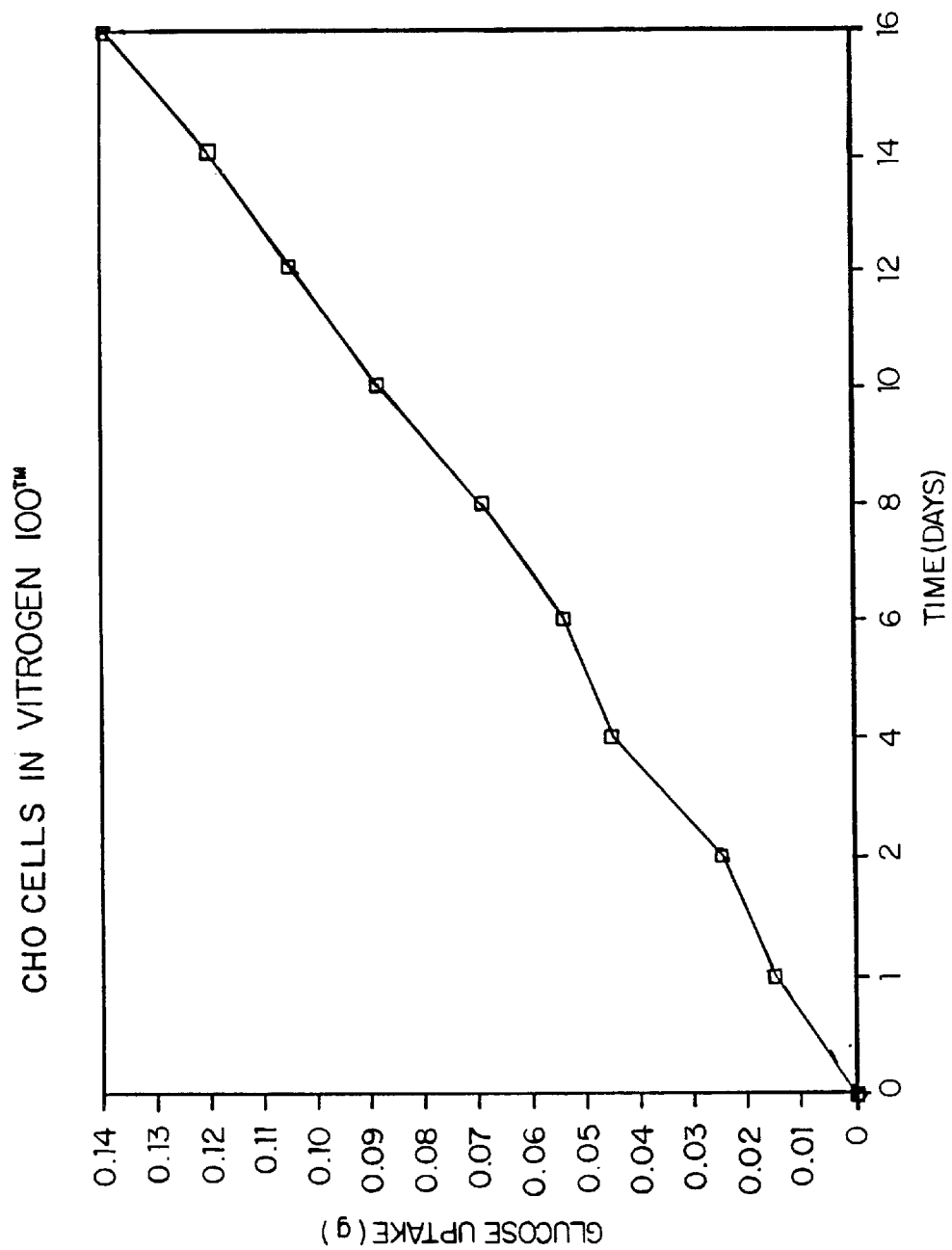
FIG. 17 is a graph.

FIGS. 13 and 16 illustrate the rapid contraction of the cell-collagen mixture as the generally dense cell-collagen matrix was formed. The hamster cells also were successfully maintained in this biocompatible matrix as shown by the glucose uptake curve of FIG. 17.

EXAMPLE 4

AFP-27 Hybridoma Cells in a Collagen Matrix

Following the general protocol of Example 1, the following modifications were made to examine AFP-27 hybridoma cells ("AFP-27 cells")in a collagen matrix. AFP-27 cells produce IgG antibody to alpha fetal protein. These cells were obtained from Dr. Robert L. Vessella at the V.A. Medical Center in Minneapolis, Minn.

The solution of Tube A included 1 ml of a double concentrated DME solution having 20% by volume horse serum; 200 units/ml Penicillin G; 200 μg/ml Streptomycin; and 0.12 ml of 0.1 N NaOH. Using the cell concentration technique set forth in Example 3, 30.8 ml of the AFP cell suspension (1.00×10$^6$ cells/ml) was concentrated to 1.03×10$^7$ cells/ml.

After Tube A and Tube B were mixed, 1.5 ml of the AFP cell suspension (1.54×10$^7$ total cells) was added to the mixture. The total mixture was poured into a petri dish and floated in a 37° C. water bath as done in Example 3. After the collagen matrix formed, 4 ml of DME containing 10% horse serum, 100 units/ml Penicillin G and 100 μg/ml Streptomycin was added to the dish. Approximately 8.0 ml of medium was changed daily.

Figure 18:
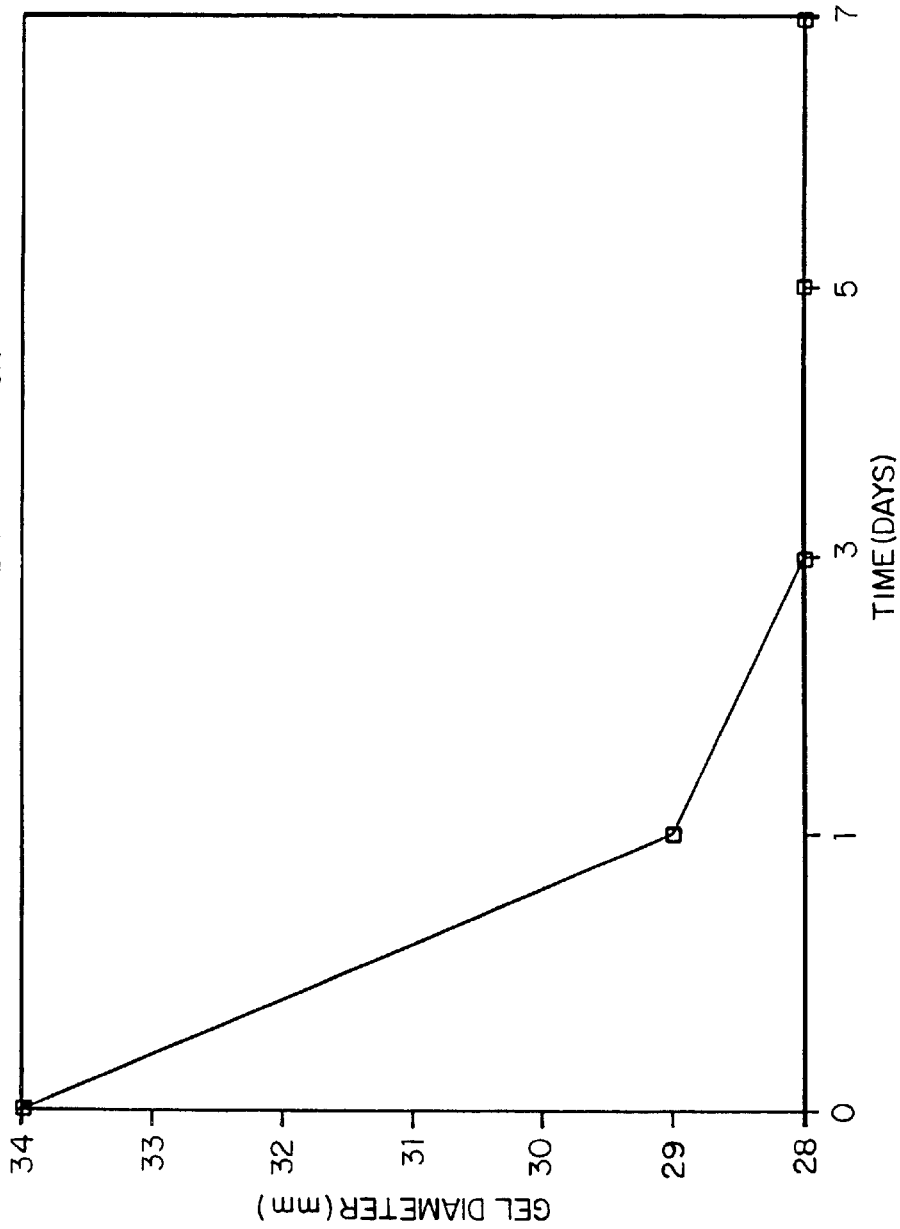
FIG. 18 is a graph.
Figure 19:
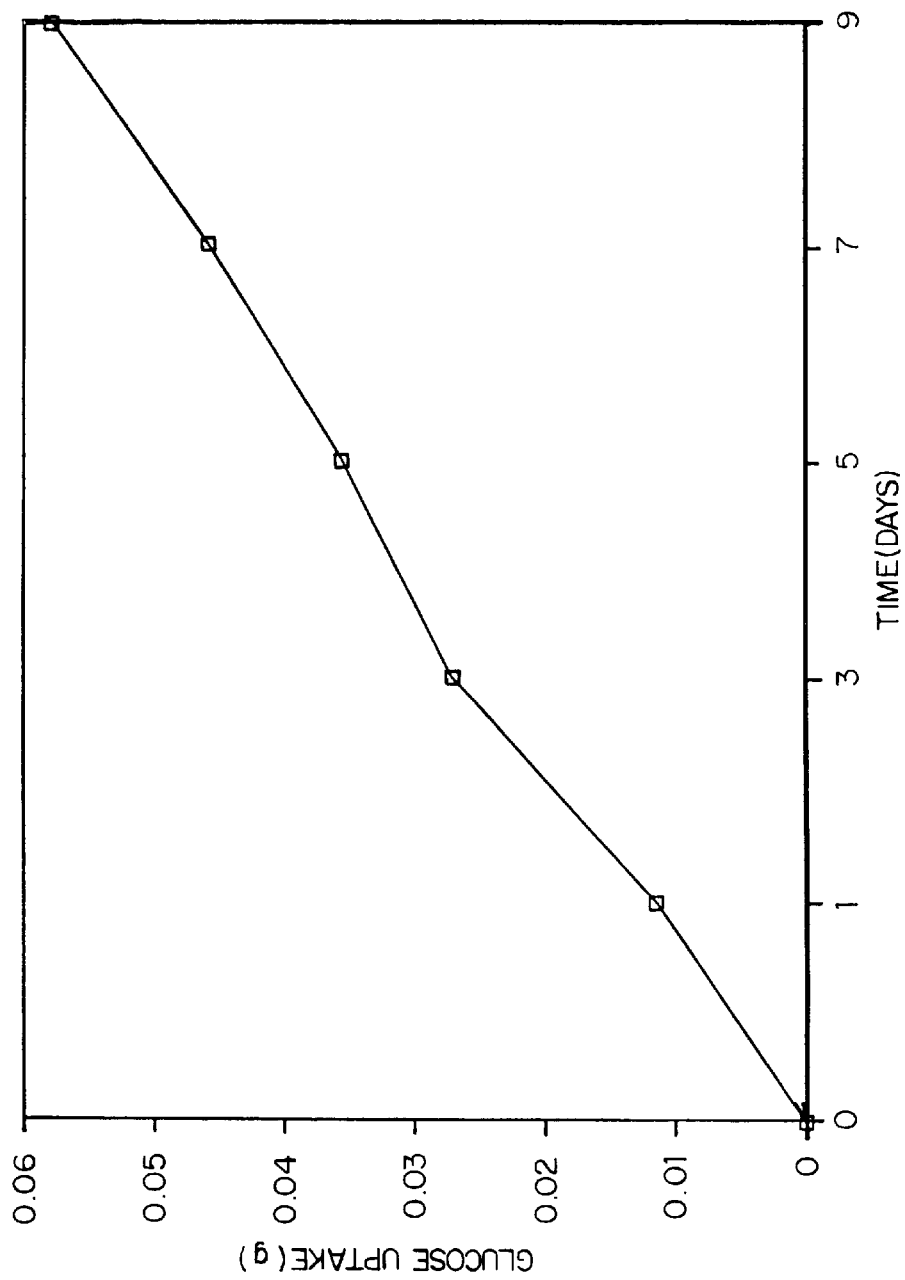
FIG. 19 is a graph.

FIGS. 13 and 18 depict the formation of the substantially insoluble cell-collagen matrix over time. FIG. 13 further compares the relative densities of the matrices formed in Examples 1, 3 and 4. The matrix of Example 3 was found to have the least diameter. The matrix of Example 4 had the largest diameter. FIG. 19 demonstrates that this cell type can be maintained in this matrix environment over a sustained time period without loss of cell viability as evidenced by the continuous glucose uptake by the entrapped cells.

EXAMPLE 5

293 Cells in a Fibrin Matrix

A solution of fibrinogen in a serum free medium was prepared by adding 0.075 g of bovine fibrinogen (Cat No. F-4753 from Sigma Chemical Co. of St. Louis, Mo.) to 15.0 ml of a modified DME/F12 solution. This modified DME/12 solution was made by mixing three parts of DME with 1 part Ham's F12 nutrient mixture (Gibco P.N. 430-1700), followed by addition of 300 μg/ml geneticin, 200 μg/ml hygromycin B and 1 μg/ml of Vitamin K (1 μg/ml). After the fibrinogen solution was mixed for 1 hour, the solution was decanted to remove any undissolved fibrinogen. The solution was then filter sterilized. A 1 unit/ml solution of thrombin was prepared by consecutive dilution of THROMBOSTAT™ in PBS. THROMBOSTAT™ is commercially available from Parke Davis in Morris Plains, N.J.

2.0 ml of the fibrinogen solution was added to Tube A. 0.2 ml of the thrombrin solution was added to Tube B. The tubes were sealed and chilled in ice water.

Using the cell suspension employed in Example 1, 0.9 ml of the cell suspension was added to Tube A and mixed. The contents of Tube B was then added to Tube A. The resulting mixture was immediately poured into a 34 mm diameter tissue culture petriplate. The plate was covered and incubated at 37° C. for 30 minutes. After incubation, 3.0 ml of the DME/F12 solution was added to the petriplate. Using these techniques, a fibrin-cell matrix was successfully formed, entrapping most of the cells, although the matrix was subsequently degraded by fibrin degrading enzymes produced by the 293 cells. However, fibrin can still be used with a variety of cell types that do not produce similar hemolytic or degrading factors, such as AFP-27 hybridoma.

These examples demonstrate how a variety of cells can be incorporated and maintained in a biocompatible, substantially insoluble matrix. Using this matrix entrapping technique, the desired cell products can be harvested without disturbing the cells allowing for continued high concentration of cell product. The substantially insoluble matrix also allows for the continuous secretion of cell product over time without interfering with cell viability.

The following example uses a matrix formed in situ in a flat bed embodiment of a bioreactor apparatus of the present invention.

EXAMPLE 6

293 Cells in a Collagen Supported Bioreactor Apparatus

Using flat bed reactor 100, which had been previously assembled and steam sterilized the following procedure was performed, again using most of the techniques described more fully in Examples 1 through 5. The contents of Tube A included 7.2 ml of twice concentrated DME solution, 10% by volume FBS and 0.48 ml 0.1 N NaOH. Tube B held 5.4 ml of VITROGEN 100™.

293 cells were trypsinized as discussed in Example 1. The resulting cell suspension had a concentration of 5.20×10$^6$ cells/ml. Using aseptic techniques, the contents of Tube A were added to Tube B, and mixed well. Immediately thereafter, the cell suspension was added to Tube B to form the matrix precursor-cell suspension. The matrix precursor-cell suspension was then quickly injected through second fluid inlet means 132 and into cell growth plate window(s) 144.

Medium reservoir 156 was filled with 300 ml of DME containing 5% by volume FBS, 300 μg/ml geneticin, 200 μg/ml hydrogromycin B and 1 μg/ml Vitamin K.

Medium was pumped from reservoir 156 through bioreactor 100. The whole apparatus was placed in a room having a temperature of approximately 37° C. Samples were taken daily from cell growth plate window 144 through a "T" valve in flow communication with second fluid outlet means 136, in order to analyze pH, glucose and cell product concentration. Cells have been maintained successfully in this apparatus for 90 days with a continual production of Protein C.

EXAMPLE 7

293 Cells in Collagen Supported Hollow Fiber Reactor

Using the hollow fiber bioreactor apparatus 200, the following procedure was conducted, again using the techniques described in Examples 1 through 5. To sterile Tube A a 7.0 ml solution was added consisting of twice concentrated DME, containing 10% by volume FBS, 600 μg/ml geneticin, 400 μg/ml hygromycin B. 2 μg/ml Vitamin K plus 0.4 ml of 0.1 N NaOH. Tube B contained 7.0 ml of VITROGEN 100™. The tubes were then placed in an ice water bath.

Hollow fiber assembly 200 was flushed with 5 l of distilled water and sterilized by immersion in distilled water with steam sterilization for 30 minutes at approximately 121° C. Reservoir 212, and all other units of the reactor were also steam sterilized. Following sterilization, the entire assembly was cooled to 4° C. and assembled aseptically in a laminar flow hood.

293 cells were trypsinized as discussed in Example 1, resulting with 5.25 ml of a cell suspension having a concentration of 1.47×10$^7$ cells/ml. Using aseptic techniques, the contents of Tube A were added to Tube B and mixed well. The resulting mixture was then immediately combined with the 293 cell suspension to form the cell-matrix precursor mixture. This cell-matrix precursor mixture was introduced into hollow fibers 210 through first fluid inlet means 202.

Figure 21:
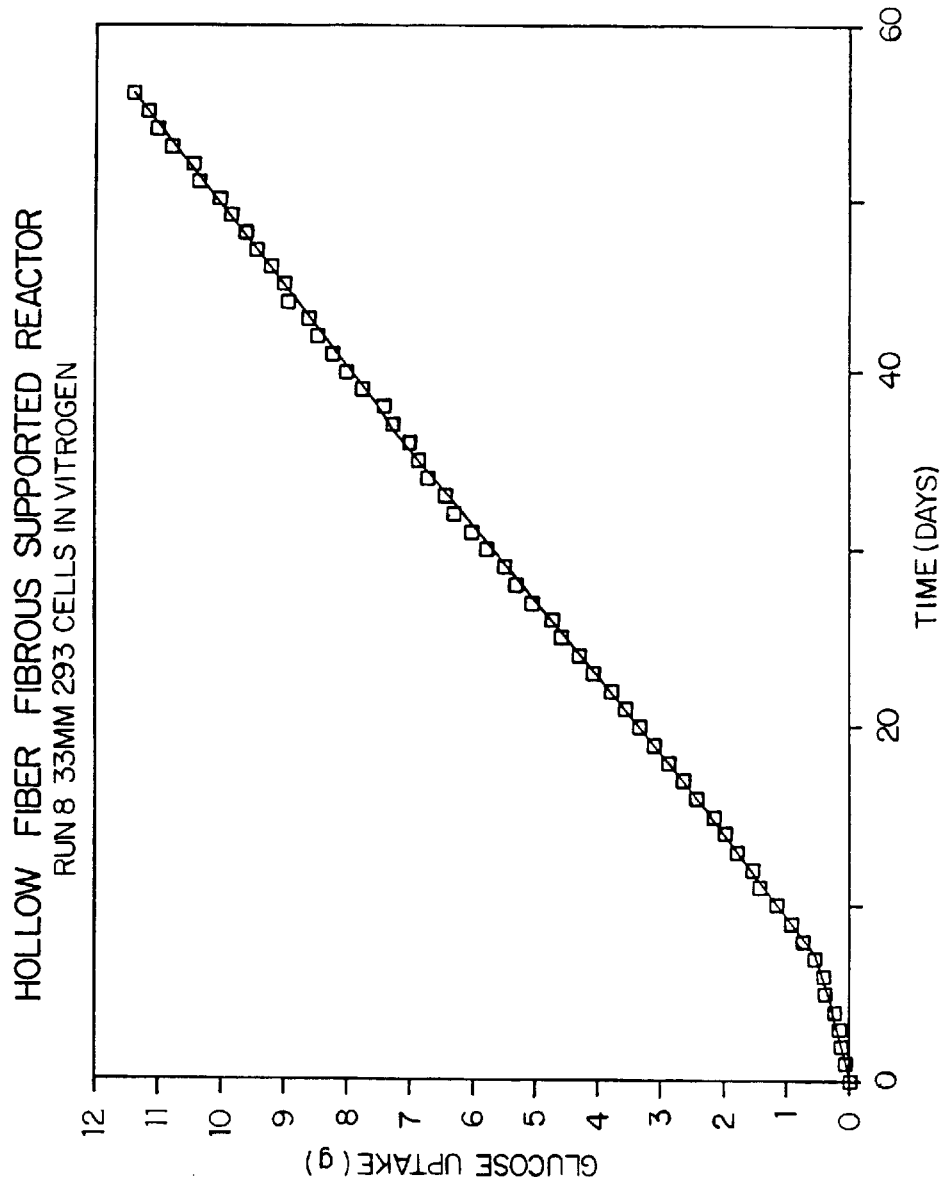
FIG. 21 is a graph.

Reservoir 212 was filled with 300 ml of DME containing 5% FBS, 300 μg/ml geneticin, 200 μg/ml hygromycin B and 1 μg/ml Vitamin K. Hydroxyethylpiperazine ethylsulfonic acid (HEPES) (8 g/l) was also added to the medium reservoir in place of sodium bicarbonate. Medium was pumped from reservoir 212 through second fluid inlet means 204, extracapillary space 216 and second fluid outlet means 208. Small samples were taken daily from first fluid inlet means 202 and analyzed for pH, glucose and Protein C concentration. Small aliquots of 1 N NaOH were added periodically to maintain the pH in the range of 7.0–7.4. Using this system, the cells were successfully maintained for 50 days (see FIG. 21). Cell product was continually collected over this time period.

B. Bioartificial Liver

Figure 24:
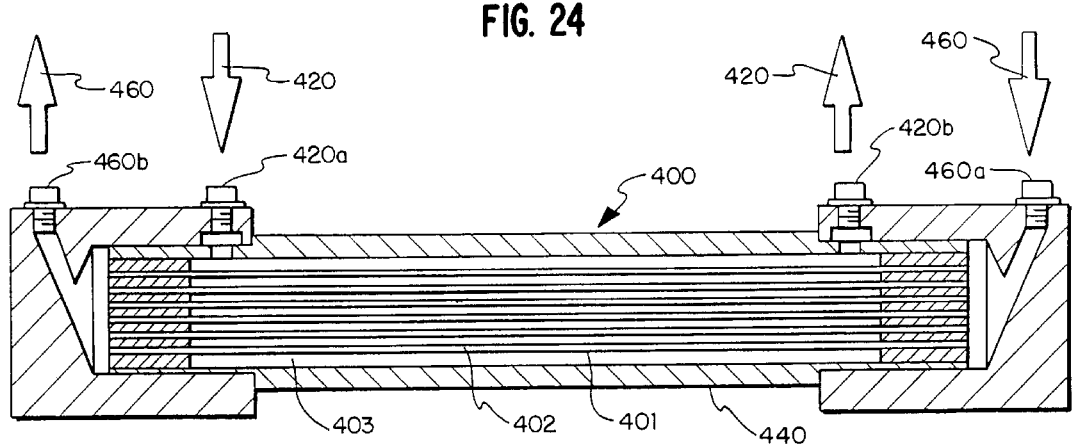
FIG. 24 is a schematic of the novel hollow fiber bioreactor employed as an artificial organ.
Figure 25:
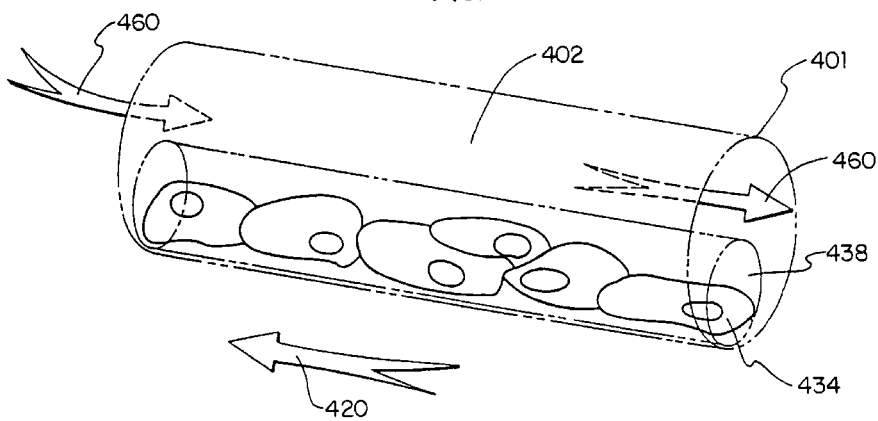
FIG. 25 is a schematic detail of a single fiber showing a contracted core of gel which contains hepatocytes.

Application of a novel bioreactor 400 including a housing 440 for cell culture as a bioartificial liver is shown in FIGS. 24 and 25 (Schultz, et al., 1990, supra). The stream (blood or plasma) to be detoxified flows through the shell side. Rather than residing in the extraluminal shell space 403, cells 434, such as hepatocytes, are within the hollow fiber lumen 402, entrapped in a gel matrix 438. This configuration is accomplished by first suspending hepatocytes 434 in a solution of collagen or a mixture of collagen and extracellular matrix components such as a mixture of collagen and heparan. The pH is then adjusted to 7.4 and the cell suspension inoculated into the lumen 402 of the hollow fiber 401. A temperature change from 4° C. to 37° C. induces collagen fiber formation. This results in cell entrapment in an insoluble fibrous and highly porous cylindrical gel 438.

After inoculation, the cross-sectional area of the gelmatrix cylinder can contract as much as 75%. This permits perfusion of hollow fiber lumen 402 even after it had been initially filled with gel matrix 438. FIG. 25 illustrates that media or blood or plasma with low molecular weight nutrients flows around hollow fibers 401 in the extraluminal shell space 403 from extraluminal inlet 420a to extraluminal outlet 420b. Molecular exchange occurs through the pores in the hollow fiber 401. Media with high molecular weight constituents flows through the hollow fiber 401 containing a contracted core of hepatocytes 434 embedded in biomatrix 438 through hollow fiber inlet 460a to hollow fiber outlet 460b.

This technique has been used with multiple cell lines including Chinese hamster ovary cells, Hep2, HepG2, Vero, 293 cells, and normal diploid human cells. Study of a hematoxylin and eosin (H & E) stained thin section of human heptoblastoma (HepG2) cells within a contracted gel matrix after 7 days showed the tissue density and cytoarchitecture closely resemble in vivo histology.

This bioreactor offers distinct advantages over other configurations. Cells can be cultured at density close to that of tissue. At high density, cells occupy much less space, thus reducing the size of the bioreactor. Cells also obtain the benefits of close contact with minimal oxygen and nutrient limitations. Mammalian cells, at high density, may better preserve tissue specific function. This has been shown in hepatoma lines. (Kelly, J. J.; Darlington, G. J. "Modulation of the liver specific phenotype in the human hepatoblastoma line HepG2". *In Vitro Cell Dev Biol*, February 1989; 25(2): 217–22).

This bioreactor configuration also allows manipulation of the hepatocytes' local environment. Matrix constituents that support differentiated hepatocyte function can be incorporated into the gel. The ability to perfuse the inner lumen provides high molecular weight growth factors at high concentrations.

Another advantage of such a system is that different cell types can be co-entrapped in the gel to provide possible synergistic effects which may improve tissue specific function.

This invention is thus capable of incorporating many factors (medium, gel matrix, co-culture, high cell density) necessary or beneficial to sustain liver specific functions. It can be used as a bioartificial liver to support patients in liver failure.

EXAMPLE 8

Hybrid Bioreactor

The new hollow fiber bioreactor 400 is illustrated in FIGS. 24 and 25. The hollow fiber 401 cartridge allows a large surface area for oxygen and nutrient exchange; cell density exceeding $10^7$ cells/ml is possible with gel entrapment.

FIG. 24 and FIG. 25 show that blood or plasma from the patient flows continuously through the extraluminal shell space 403 and semi-permeable hollow fibers 401 which separate this fluid from the hepatocytes 434. Intraluminal stream 460 containing high molecular weight constituents flow through hollow fibers 401 containing hepatocytes 434 in biomatrix 438. The extraluminal stream 420 containing the patient's blood or plasma flows in either a countercurrent, cross-current, or co-current direction to the intraluminal stream 460. Molecular exchange occurs through the pores in the hollow fiber 401. It is probable that blood— particularly from a patient in liver failure—does not provide the optimal chemical environment to sustain hepatocyte function and viability. Intraluminal stream 460 containing growth factors and nutrients is passed through the hollow fiber lumen. Intraluminal stream 460 can also provide toxin or metabolic product removal.

This two channel hollow fiber design supplies both a "life support system" for the hepatocytes 434, and a stream of waste products. The selectively permeable hollow fibers 401 can allow diffusion of waste products, such as ammonia and bilirubin from the blood, for detoxification and/or biotransformation by the hepatocytes. Waste products are then cleared in the hollow fiber intraluminal stream 460. These conditions can result in improved hepatocyte survival and continuous function.

Several fundamental aspects of hepatocyte cultivation have been addressed. Prolonged hepatocyte viability and function have been demonstrated in monolayer cultures. The contraction of three-dimensional collagen gels and rat hepatocytes has also been demonstrated. Energy metabolism and bilirubin conjugation by hepatocytes in these contracted gels have been shown. Finally, viable and functional hepatocytes within the bioreactor have been demonstrated through vital dyes, oxygen consumption, glucose consumption, and bilirubin conjugation.

EXAMPLE 9

Three-Dimensional Collagen Gels

In order to achieve a high cell density and simulate a natural environment, hepatocytes were cultured in three dimensional collagen gels. Dime-sized collagen "discs" and thin diameter cylindrical collagen "cores" of 0.5 or 1.1 mm in diameter were evaluated. Gels contained 2 gm/l of Type I collagen in isotonic DMEM. Collagen gel discs were made by adding a mixture of collagen/DMEM and hepatocytes to empty tissue culture plates. Collagen gels have been made with other isotonic media, such as Williams' E medium. Media was added following gel formation. Silicone tubing was used to form thin diameter collagen gel cores. After 10 minutes of incubation at 37° C., the cylindrical gel cores were extruded into media containing wells. All collagen gel experiments including bioreactor trails were done using Williams' E medium supplemented with 10% calf serum, insulin, L-glutamine (Modified Williams' E medium) or a serum-free hormonally defined media. (Lanford, supra).

Gel Contraction Measurements

Figure 26:
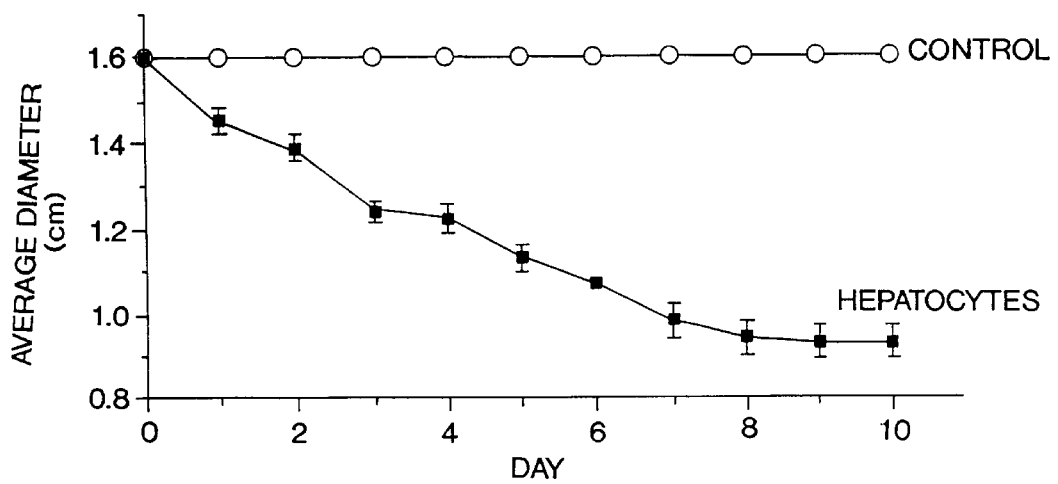
FIG. 26 illustrates the contraction in hepatocyte gel discs.

Collagen gel discs were used to assess gel contraction. Many combinations of gel thickness and cell density were compared. Gel diameters were measured daily for 10 days and the average of greatest width and its perpendicular width was recorded. FIG. 26 summarizes the average daily gel contraction resulting from several hepatocyte cultures. Gel discs containing dead cells or no cells were used as controls. Error bars show standard error. Control gels without cells or with dead cells did not contract. Thus, gel contraction becomes a criterion for viability. The cell concentrations tested ranged from 0.2 to $2.0 \times 10^7$ cells/ml of gel. Both cell density and gel thickness effected the rates of contraction. The examples shown in FIG. 26 had an average decrease in diameter of 40% at ten days, which corresponds to a 64% reduction in cross-sectional area. Further studies were carried out in hollow fibers. After contraction, the collagen matrix leaves a residual lumen of sufficient size to allow growth factor, media, or waste stream perfusion.

Metabolic Results in Gel

Collagen gel cores were used to measure metabolic activity. After formation in the silicone tubing, the gel cores were placed in spinner flasks and incubated for 30 hours. Media samples were taken for analysis at six hour intervals.

Figure 27:
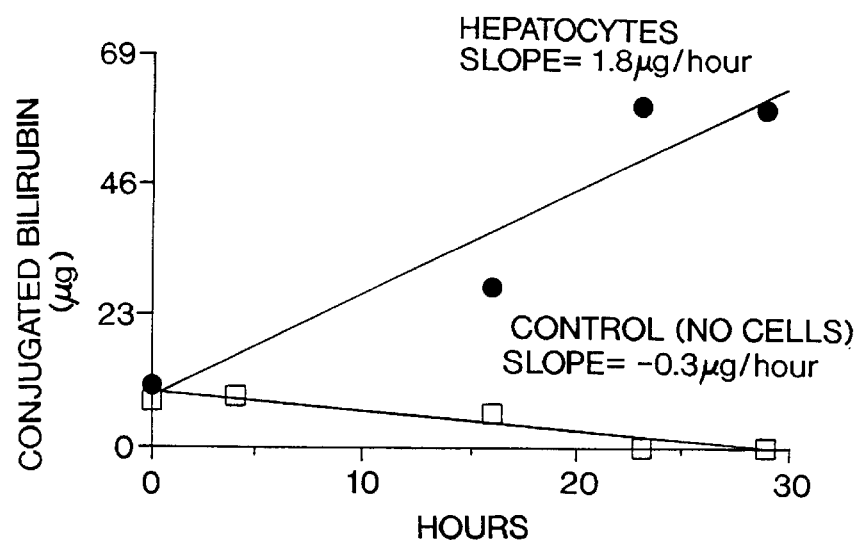
FIG. 27 illustrates the bilirubin conjugation rate in spinner flasks containing hepatocyte-gel cores.

A glucose consumption rate of 1.1 mg/hour was calculated for gels containing $2.3 \times 10^7$ hepatocytes. Glucose consumption was negligible in the control spinner flasks that contained media and gels without cells. Bilirubin conjugation, a function unique to hepatocytes and catalyzed by UDP glucuronosyl transferase, was measured by high performance liquid chromatography (HPLC). (FIG. 27). A conjugation rate of 1.8 µg/hour was measured by linear regression analysis. The level of conjugated bilirubin remained negligible in the control gels without cells.

EXAMPLE 10

Hollow Fiber Reactor Apparatus

A hollow-fiber system assembly consisted of an Amicon H1 hollow-fiber cartridge with Delrin end caps. The hollow fibers were made of porous polysulfone with a 30,000 molecular weight cut-off. The extracapillary space (outer shell) was perfused with Modified Williams' E medium. The inner channel was not perfused. The hollow fiber reactor was kept in a 37° C. warm room following inoculation.

Metabolic Results

The following results relate to the hepatocyte hollow-fiber reactor. $1.20 \times 10^8$ rat hepatocytes at a final concentration of $0.9 \times 10^7$ cells/ml of gel were cultured for 120 hours. Partial pressure of oxygen was measured in the inflow and the outflow streams, and oxygen uptake rate (OUR) was calculated from the following equation:

$$OUR = [C_{in} - C_{out}]F$$

$C_{in}$ is the inlet oxygen concentration;
$C_{out}$ is the outlet oxygen concentration;
F is the media flow rate.

The oxygen uptake rate increases with increasing flow rate at low flow rates, and becomes flow independent at high flow rates. A flow rate of 30 ml/min was sufficient to maintain maximum oxygen uptake without inducing the larger pressure drop seen at higher flow rates, and was used in this example.

Figure 28:
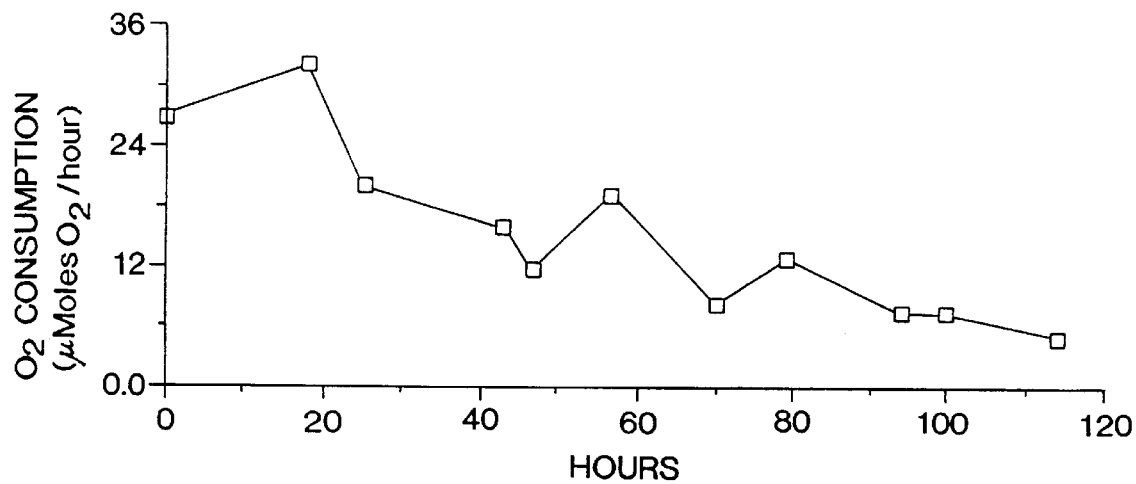
FIG. 28 illustrates the oxygen consumption rate in the hollow fiber bioreactor over 120 hours.

The oxygen consumption rose during the first 20 hours and then declined gradually until termination at 120 hours. (FIG. 28). Glucose concentration in the perfused media was measured by a spectrophotographic assay. Glucose consumption rate as determined by linear regression was 1.0 mg/hour. Judging from the consumption of oxygen and glucose, hepatocytes cultivated in this bioreactor were metabolically active.

Bilirubin Clearance

Figure 29:
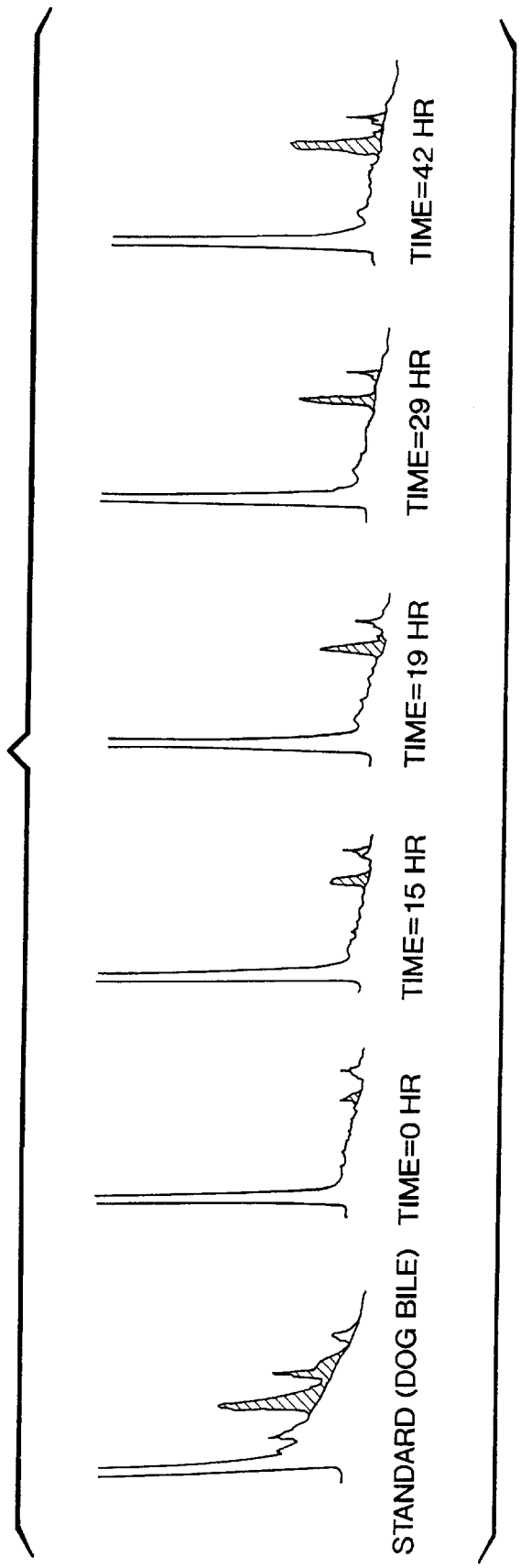
FIG. 29 is an HPLC analysis of bilirubin.
Figure 30:
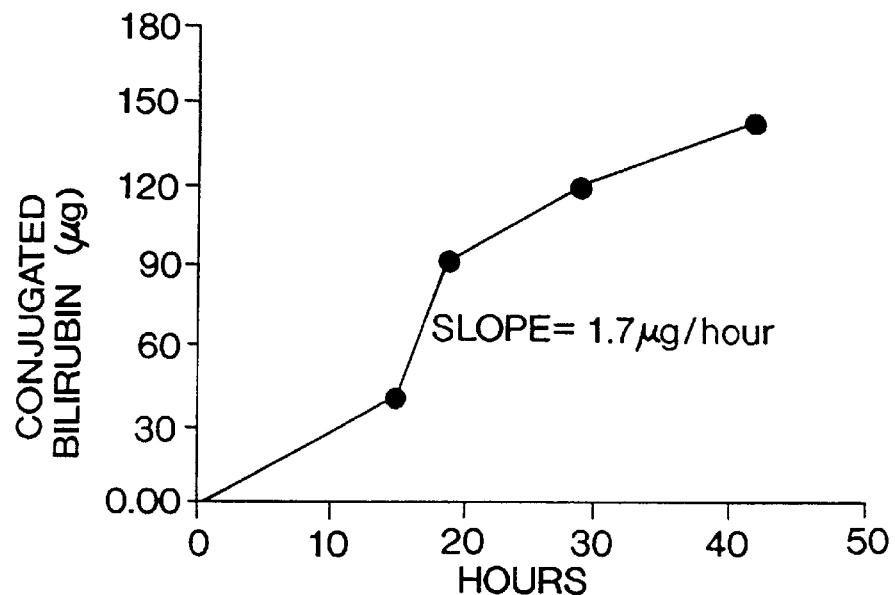
FIG. 30 illustrates bilirubin conjugation (HPLC) data.
Figure 31:
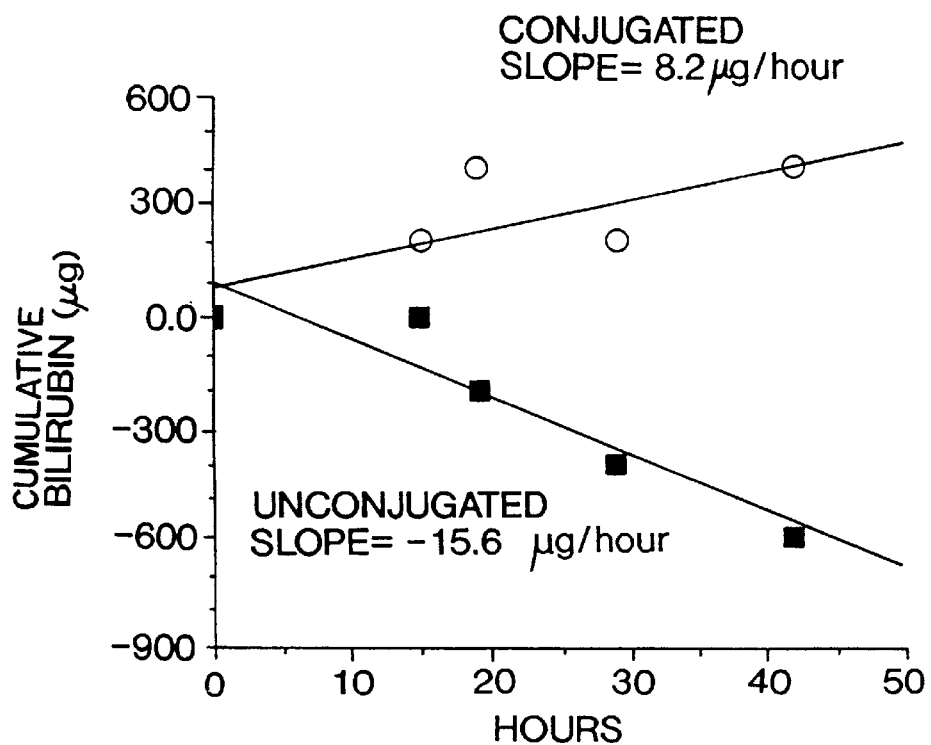
FIG. 31 illustrates conjugated and unconjugated bilirubin levels (Ektachem 700XR).

Perfusion of this same bioreactor with fresh media containing unconjugated bilirubin at 2.1 mg/dl was begun at 40 hours (t=0) and continued for 42 hours. Samples were taken from the media circulating on the shell side. Bilirubin conjugation was measured by both HPLC and Kodak Ektachem absorbance. A significant conjugation rate was detected by both techniques. This accumulation of conjugated bilirubin can be visualized from the raw HPLC data; monoconjugate and diconjugate peaks are shaded (FIG. 29). Bilirubin conjugation rates of 1.7 pg/hour and 8.2 µg/hour were obtained by linear regression analysis of HPLC (FIG. 30) and Ektachem data (FIG. 31), respectively. Unconjugated bilirubin levels are also included on FIG. 31. Judging from the appearance of conjugated bilirubin in the medium, hepatocytes cultivated in the hollow fiber bioreactor are capable of liver specific function—namely, bilirubin conjugation.

While many specific embodiments have been shown and described in detail to illustrate the application of the principles of this invention, it will be understood by those skilled in the art that the invention may be embodied otherwise without departing from such principles. For example, while the hollow fiber assembly was described using a conventional nutrient medium flow traveling along the length of the hollow fibers in the extracapillary space, a crossflow system may also be used such that nutrient medium would flow generally perpendicular to the hollow fibers. Indeed, a crossflow system may provide a higher oxygen transfer to a greater proportion of entrapped cells.

Further, a novel bioreactor system for short term support in cases of liver failure is provided. A system using the gel matrix concepts described herein provides constant optimal media perfusion to detoxify blood and facilitates liver cell metabolic function. A device using this concept is designed such that the blood flow and media flow allow proper oxygenation, toxin transfer, and toxin-metabolite removal. Likewise, membrane pore size allows proper diffusion rates for toxin removal and liver cell metabolic function.

Further, while many specific embodiments of the bioartificial liver have been shown and described in detail to illustrate the application of the principles of this invention, it again will be understood by those skilled in the art that the invention may be embodied otherwise without departing from such principles. For example, while a hollow fiber system is described herein using the gel matrix/biomatrix concept, a flatbed bioreactor could be used. A suitable flat-bed reactor is shown in FIGS. 5–10. In such a system, the entrapped cells would be hepatocytes. Moreover, a cell gel matrix other than collagen may be employed such as Type III collagen, chitosan or fibronectin. The selected material need only be biocompatible and capable of forming a cell gel matrix.

What is claimed is:

1. A method for maintaining animal cells and genetically altered derivative cells thereof in vitro over a sustained period of time for continuous production of a desired cell product comprising the steps of:
   (a) introducing a matrix precursor including said cells into a cell chamber;
   (b) inducing said matrix precursor including said cells to form an insoluble cell-biocompatible matrix means including said cells;
   (c) contracting said insoluble cell-biocompatible matrix means including said cells in situ within said cell chamber approximately one-third of the original volume occupied within said cell chamber by said matrix precursor and said cells to form a contracted insoluble matrix entrapping said cells and another chamber comprising a liquid phase for accumulating the desired cell product;
   (d) supplying nutrient medium of said cells by passing said nutrient medium through an inlet means leading to a chamber for cell nutrient and cell waste, said chamber for cell nutrient and cell waste separated from said cell chamber by a selectively permeable membrane, and perfusing said nutrient medium through said membrane into said cell chamber;
   (e) withdrawing expended nutrient medium and cell waste which have traveled from said cell chamber to said chamber for cell nutrient and cell waste through said permeable membrane from the chamber for cell nutrient and cell waste through an outlet means; and
   (f) withdrawing the desired cell product from said cell chamber through a second outlet means in flow communication with said cell chamber.

2. The method of claim 1, wherein said matrix means is formed from teleopeptide native collagen, ateleopeptide native collagen or modified collagen.

3. The method of claim 1, wherein said membrane is a processed cellulose derivative which is permeable to low molecular weight nutrient and cell waste product compounds, impermeable to high molecular weight desired cell product compounds, and has an upper molecular weight permeability limit equal to or less than that of desired cell product.

4. The method of claim 1, wherein said membrane is one of polysulfone, Teflon® and ceramic.

5. The method of claim 1, wherein said matrix means is formed from a collagen-chitosan mixture.

6. The method of claim 1, wherein said matrix means is formed from fibrin.

7. The method of claim 1, wherein said selectively permeable membrane allows the passage of compounds having a molecular weight below about 12,000.

8. The method of claim 1, wherein said selectively permeable membrane allows the passage of compounds having a molecular weight below about 30,000.

9. The method of claim 1, wherein said selectively permeable membrane allows the passage of compounds having a molecular weight below about 100,000.

10. The method of claim 1, wherein said cells are Chinese hamster ovary cells.

11. The method of claim 1, further comprising introducing serum free medium as said nutrient medium into said chamber for cell nutrient and cell waste such that cell viability is maintained as is determinable through detection of no substantial decrease in glucose consumption rate of said cells.

12. The method of claim 1, wherein said cells are hybridoma cells.

13. The method of claim 1, further comprising adding protein free cell culture medium as said nutrient medium into said chamber for cell nutrient and cell waste.

14. A method of supporting hepatocyte function and viability for treating a patient suffering from hepatic failure comprising the steps of:
   (a) introducing a matrix precursor including hepatocytes into a cell chamber;
   (b) inducing said matrix precursor including said hepatocytes to form an insoluble hepatocyte-biocompatible matrix means including said hepatocytes:
   (c) contracting said insoluble hepatocyte-biocompatible matrix means including said hepatocytes in situ within said cell chamber approximately one-third of the original volume occupied within said cell chamber by said matrix precursor and said hepatocytes to form a contracted insoluble matrix entrapping said hepatocytes and another chamber comprising a liquid phase within said cell chamber;
   (d) supplying a fluid flow of blood or plasma from said patient through a first fluid flow means to said cell chamber containing said contracted insoluble matrix entrapping said hepatocytes such that communication between said blood or plasma and said hepatocytes is exclusively through a selectively permeable membrane to allow diffusion of waste products through said membrane from said blood or plasma for detoxification by said hepatocytes; and
   (e) supplying a fluid flow of a hepatocyte support medium containing growth factors for said hepatocytes through a second fluid flow means such that said medium flows through said another chamber in said cell chamber in contact with said contracted insoluble matrix entrapping said hepatocytes and separated from said blood or plasma by said membrane to effect hepatocyte waste removal and support hepatocyte function and viability.

15. The method of claim 14, wherein said blood or plasma flow and said hepatocyte support medium flow are continuous and counter-current to each other.

16. The method of claim 14, wherein said blood or plasma flow and said hepatocyte support medium flow are continuous or intermittent and co-current or cross-current or counter-current to each other.

17. The method of claim 14, wherein said selectively permeable membrane means comprises hollow fibers and contracted insoluble matrix entrapping said hepatocytes is within the hollow fiber lumen.

18. The method of claim 14, wherein said selectively permeable membrane means comprises a membrane forming a cell chamber, and said cell chamber contains the contracted insoluble matrix entrapping said hepatocytes.

19. A method of preserving tissue-specific function of mammalian cells comprising the steps of:
   (a) introducing a matrix precursor including said mammalian cells into a cell chamber;
   (b) inducing said matrix precursor including said cells to form an insoluble cell-biocompatible matrix means including said cells;
   (c) contracting said insoluble cell-biocompatible matrix means including said cells in situ within said cell chamber approximately one-third of the original volume occupied within said cell chamber by said matrix precursor and said cells to form a contracted insoluble matrix entrapping said cells and another chamber comprising a liquid phase within said cell chamber;

(d) supplying a fluid flow of perfusing medium through a first fluid flow means to said cell chamber containing said contracted insoluble matrix entrapping said cells such that communication between said perfusing medium and said cells is exclusively through a selectively permeable membrane to support cell function and viability of said cells; and (e) supplying a fluid flow of liquid medium through a second fluid flow means such that said liquid medium flows through said another chamber within said cell chamber in contact with said contracted insoluble matrix entrapping said cells and separated from said perfusing medium by said membrane to effect waste removal and support cell function and viability.

20. The method of claim 19, wherein said contracted insoluble matrix entrapping said cells is maintained within the lumen of hollow fibers and communication between said cells and said perfusing medium is through said hollow fiber walls.

21. The method of claim 19, wherein said contracted insoluble matrix entrapping said cells is maintained within a cell chamber created by a membrane and communication between said cells and said perfusing medium is through said membrane.

22. The method of claim 19, wherein the mammalian cells are pancreatic islet cells, bone marrow stem cells, liver cells or liver tumor cells.

* * * * *